US012569137B2

(12) United States Patent (10) Patent No.: US 12,569,137 B2
Yamanari et al. (45) Date of Patent: Mar. 10, 2026

(54) OPHTHALMIC DEVICE

(71) Applicant: Tomey Corporation, Nagoya (JP)

(72) Inventors: Masahiro Yamanari, Nagoya (JP);
Keiichiro Okamoto, Nagoya (JP)

(73) Assignee: Tomey Corporation, Nagoya (JP)

( * ) Notice: Subject to any disclaimer, the term of this
patent is extended or adjusted under 35
U.S.C. 154(b) by 353 days.

(21) Appl. No.: 18/202,170

(22) Filed: May 25, 2023

(65) Prior Publication Data

US 2023/0380691 A1 Nov. 30, 2023

(30) Foreign Application Priority Data

May 27, 2022 (JP) ................................. 2022-087144

(51) Int. Cl.
*A61B 3/10* (2006.01)
*A61B 3/14* (2006.01)
(Continued)

(52) U.S. Cl.
CPC .......... *A61B 5/0062* (2013.01); *A61B 3/1005*
(2013.01); *A61B 3/102* (2013.01); *A61B*
*3/0025* (2013.01); *G01B 9/02091* (2013.01)

(58) Field of Classification Search
CPC ..... A61B 3/1005; A61B 3/102; A61B 3/0025;
A61B 5/0062; G01B 9/02091
(Continued)

(56) References Cited

U.S. PATENT DOCUMENTS

2007/0076217 A1* 4/2007 Baker .................. A61B 3/1005
356/497
2012/0200827 A1 8/2012 Kato et al.
(Continued)

FOREIGN PATENT DOCUMENTS

CN 215348886 U 12/2021
JP 2012-161425 A 8/2012
(Continued)

OTHER PUBLICATIONS

Xuan Wang et al. "A simple system of swept source optical
coherence tomography for a large imaging depth range", Optics
Communications, 2018.

*Primary Examiner* — Mahidere S Sahle
(74) *Attorney, Agent, or Firm* — Jason A. Smith;
Shumaker, Loop & Kendrick, LLP

(57) ABSTRACT

An ophthalmic device that may include: a light source; a
measurement optical system that generates measurement
light; a first reference optical system that generates first
reference light; a second reference optical system that gen-
erates second reference light; and an interference optical
system that generates measurement interference light from
the measurement light and the first reference light, and
reference interference light from the first and second refer-
ence light. The measurement optical system may include a
switching unit that switches between a first state in which the
subject eye is irradiated with the light from the light source
and a second state in which the light from the light source
is guided to the second reference optical system branching
from the measurement optical system. The controller may
control the switching unit to detect the measurement inter-
ference light in the first state, and the reference interference
light in the second state.

15 Claims, 7 Drawing Sheets

(51) Int. Cl.
    *A61B 5/00*        (2006.01)
    *A61B 3/00*        (2006.01)
    *G01B 9/02091*    (2022.01)

(58) Field of Classification Search
    USPC ........................................ 351/206, 221, 246
    See application file for complete search history.

(56)              References Cited

U.S. PATENT DOCUMENTS

| | | |
|---|---|---|
| 2014/0125951 A1 | 5/2014 | Eom et al. |
| 2015/0320309 A1 | 11/2015 | Kato et al. |
| 2018/0279873 A1 | 10/2018 | Kato et al. |
| 2020/0100674 A1 | 4/2020 | Yamanari et al. |

FOREIGN PATENT DOCUMENTS

| | | |
|---|---|---|
| JP | 2016022010 A | 2/2016 |
| JP | 2020054480 A | 4/2020 |
| WO | 2016009604 A1 | 1/2016 |

* cited by examiner

OPHTHALMIC DEVICE

CROSS-REFERENCE TO RELATED APPLICATION

The present application claims priority to Japanese Patent Application No. 2022-087144, filed on May 27, 2022, the entire contents of which are incorporated herein by reference.

TECHNICAL FIELD

The disclosure herein relates to ophthalmic devices configured to capture tomographic images of a subject eye using an optical interference phenomenon.

BACKGROUND ART

In an ophthalmic device that uses an optical interference phenomenon, reference light and measurement light are combined to generate measurement interference light, and depthwise position information of a subject eye is calculated from the generated measurement interference light (for example, Japanese Patent Application Publication No. 2012-161425).

SUMMARY

In order to accurately calculate depthwise position information in this type of ophthalmic device, an optical path length of an optical system that generates reference light and measurement light needs to be adjusted accurately. For this purpose, calibration on the optical system is performed at the time of manufacture of the ophthalmic device, and the device is thereafter shipped out (that is, a calibration process is performed at the time of shipping (more precisely, at the time of optical system calibration incorporated in a manufacturing procedure)). However, due to changes that occur in the optical path length of the optical system due to post-shipment chronological change and/or an environment (such as temperature) at the time of measurement, there are cases in which measurement under the same condition as the calibration process is difficult to achieve. To address this, consideration may be given to correcting the depthwise position information of the subject eye by generating reference light, which will be referred to as "correction reference light", by splitting a part of light in an interference optical system and using this correction reference light.

However, with such an ophthalmic device, a part of light from a measurement optical system is emitted onto the subject eye to generate measurement light, and also a part of the light from the measurement optical system is split to generate correction reference light. Then, depthwise position information of the subject eye calculated from the measurement light is corrected using a reference position calculated from the correction reference light. Due to this, there is a restriction that the reference position calculated from the correction reference light needs to be set to a position different from that of the depthwise position information of the subject eye calculated from the measurement light. The disclosure herein discloses art capable of setting a reference position calculated from correction reference light at a desired position in an ophthalmic device that corrects depthwise position information of the subject eye using the correction reference light.

A first ophthalmic device disclosed herein may comprise: a light source; a measurement optical system configured to generate measurement light by irradiating a subject eye with light from the light source; a first reference optical system configured to generate first reference light by using the light from the light source; a second reference optical system configured to generate second reference light by using the light from the light source, the second reference light being used for calculating a reference position; an interference optical system configured to generate measurement interference light by combining the measurement light and the first reference light and to generate reference interference light by combining the second reference light and the first reference light; a detector configured to detect the measurement interference light and output a measurement interference signal and to detect the reference interference light and output a reference interference signal; and a controller configured to calculate depthwise position information of the subject eye based on the measurement interference signal and to calculate the reference position based on the reference interference signal. The second reference optical system may include an optical path branching from the measurement optical system. The measurement optical system may comprise a switching unit configured to switch between a first state and a second state, the first state being a state in which the subject eye is irradiated with the light from the light source and the second state being a state in which the light from the light source is guided to the second reference optical system, and when the subject eye is measured, the controller may be configured to control the switching unit to detect the measurement interference light with the detector in the first state, and to detect the reference interference light with the detector in the second state.

A second ophthalmic device disclosed herein may comprise: a first OCT configured to measure a first depthwise position of a first part of a subject eye; a second OCT configured to measure a second depthwise position of a second part of the subject eye, the second part being different from the first part; and a controller configured to calculate a depthwise length from the first part to the second part based on the first depthwise position measured by the first OCT and the second depthwise position measured by the second OCT. The first OCT may comprise: a first light source; a first measurement optical system configured to generate first measurement light by irradiating the first part of the subject eye with light from the first light source; a first reference optical system configured to generate first reference light by using the light from the first light source; a second reference optical system configured to generate second reference light by using the light from the first light source, the second reference light being used for calculating a first reference position; a first interference optical system configured to generate first measurement interference light by combining the first measurement light and the first reference light and to generate first reference interference light by combining the second reference light and the first reference light; and a first detector configured to detect the first measurement interference light and output a first measurement interference signal and to detect the first reference interference light and output a first reference interference signal. The second reference optical system may include an optical path branching from the first measurement optical system, the first measurement optical system my comprise a first switching unit configured to switch between a first state and a second state, the first state being a state in which the subject eye is irradiated with the light from the first light source and the second state being a state in which the light from the first light source is guided to the second reference optical system, and when the subject eye is measured, the first detector may be configured to detect the first measurement interference light while the first switching unit is in the first state, and to detect the first reference interference light while the first switching unit is in the second state.

DETAILED DESCRIPTION

Figure 1:
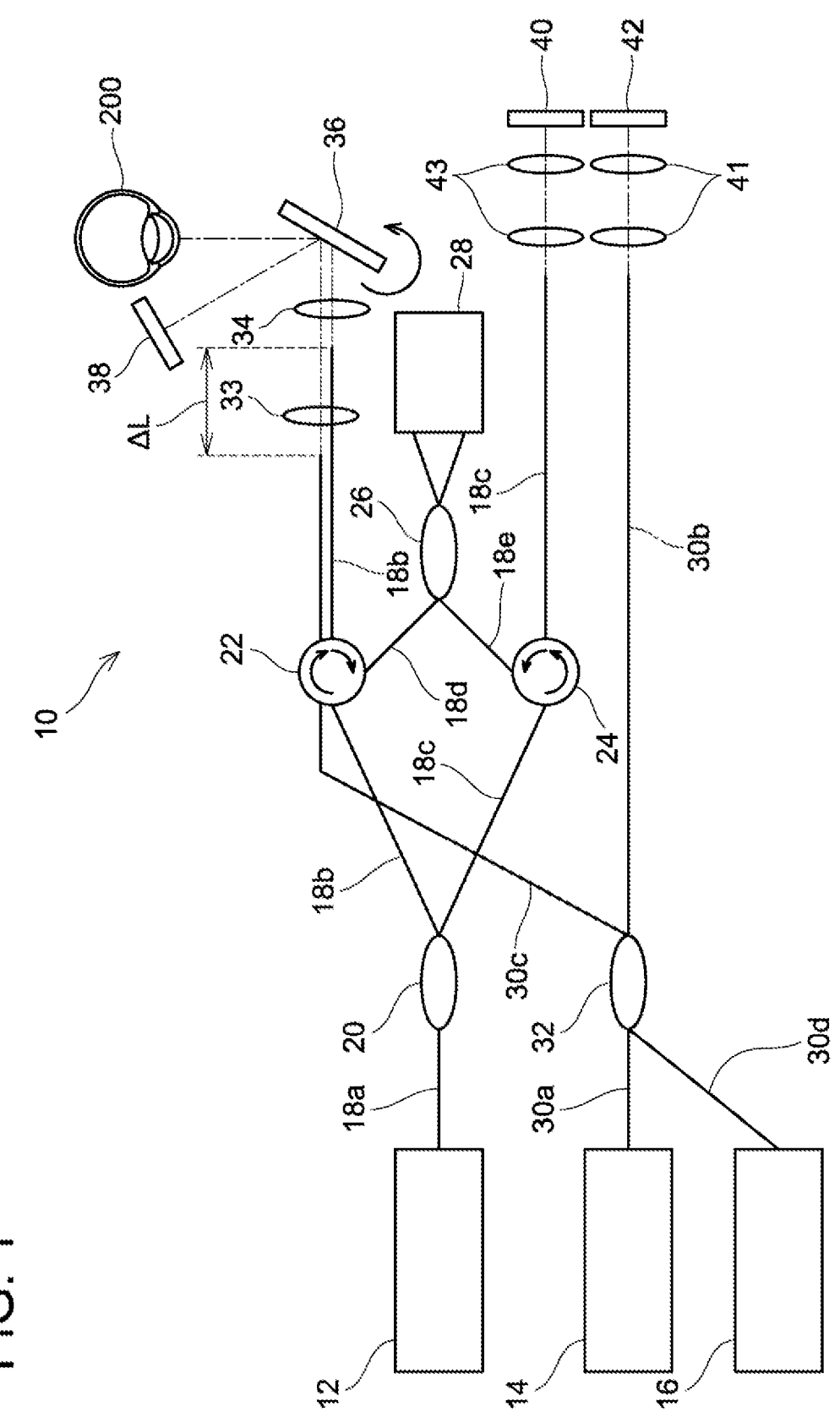
FIG. 1 shows a configuration of optical systems of an ophthalmic device according to a first embodiment.

Representative, non-limiting examples of the present disclosure will now be described in further detail with reference to the attached drawings. This detailed description is merely intended to teach a person of skill in the art further details for practicing preferred aspects of the present teachings and is not intended to limit the scope of the present disclosure. Furthermore, each of the additional features and teachings disclosed below may be utilized separately or in conjunction with other features and teachings to provide improved ophthalmic devices, as well as methods for using and manufacturing the same.

Moreover, combinations of features and steps disclosed in the following detailed description may not be necessary to practice the present disclosure in the broadest sense, and are instead taught merely to particularly describe representative examples of the present disclosure.

Furthermore, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

Some of primary features of the first ophthalmic device and the second ophthalmic device as described above will be listed. The technical elements described hereinbelow are each independent and capable of achieving technical usefulness alone or in various combinations, and such combinations are not limited to those recited in the claims as originally filed.

A first ophthalmic device disclosed herein may comprise: a light source; a measurement optical system configured to generate measurement light by irradiating a subject eye with light from the light source; a first reference optical system configured to generate first reference light by using the light from the light source; a second reference optical system configured to generate second reference light by using the light from the light source, the second reference light being used for calculating a reference position; an interference optical system configured to generate measurement interference light by combining the measurement light and the first reference light and to generate reference interference light by combining the second reference light and the first reference light; a detector configured to detect the measurement interference light and output a measurement interference signal and to detect the reference interference light and output a reference interference signal; and a controller configured to calculate depthwise position information of the subject eye based on the measurement interference signal and to calculate the reference position based on the reference interference signal. The second reference optical system may include an optical path branching from the measurement optical system. The measurement optical system may comprise a switching unit configured to switch between a first state and a second state, the first state being a state in which the subject eye is irradiated with the light from the light source and the second state being a state in which the light from the light source is guided to the second reference optical system, and when the subject eye is measured, the controller may be configured to control the switching unit to detect the measurement interference light with the detector in the first state, and to detect the reference interference light with the detector in the second state.

The above ophthalmic device is switched between the first state in which the light from the light source is emitted onto the subject eye and the second state in which the light from the light source is guided to the second reference optical system. When the subject eye is measured, the measurement interference light is detected with the detector in the first state and the reference interference light is detected with the detector in the second state. That is, the period for detecting the measurement interference light and the period for detecting the reference interference light are different. Due to this, the reference position calculated from the reference interference signal can be set to a desired position irrelevant to the depthwise position information of the subject eye that is calculated from the measurement interference signal.

(First aspect) In the first ophthalmic device disclosed herein, the controller may be configured to control the switching unit to detect the reference interference signal with the detector in the second state before or after detecting the measurement interference light with the detector in the first state. According to this configuration, the reference position is obtained before or after the depthwise position information of the subject eye is obtained. Due to this, the depthwise position information of the subject eye can be corrected by suitably taking into consideration the situation at the time of the measurement.

(Second aspect) In the first ophthalmic device or the first aspect disclosed herein, the ophthalmic device may further comprise a storage unit configured to store a specific-time reference position indicating the reference position adjusted at a specific time, the specific-time reference position being a position calculated from the reference interference light generated by combining the second reference light generated in the second reference optical system and the first reference light generated in the first reference optical system at the specific time. The controller may be configured to correct the depthwise position information of the subject eye calculated based on the measurement interference signal outputted from the detector when the subject eye is measured, the depthwise position information being corrected based on a difference between a measurement-time reference position and the specific-time reference position stored in the storage unit, the measurement-time reference position being the reference position calculated based on the reference interference signal outputted from the detector when the subject eye is measured. According to this configuration, the depthwise position information of the subject eye is corrected based on the reference position obtained at the time of the measurement and the reference position obtained at the specific time (such as, pre-shipping calibration or repair calibration). Due to this, chronological changes that may occur in the optical systems between the specific time and the measurement can be taken into consideration.

(Third aspect) In the second aspect of the first ophthalmic device disclosed herein, the storage unit may be configured to further store a conversion formula for converting the depthwise position information of the subject eye calculated based on the measurement interference signal to an actual measurement of the subject eye, the controller may be configured to further calculate the actual measurement of the subject eye by converting the depthwise position information of the subject eye calculated based on the measurement interference signal with the conversion formula, and the conversion formula may be obtained by using (A) depthwise position information of at least two reflection surfaces of a calibration tool having a known optical path length difference and (B) the optical path length difference between the at least two reflection surfaces, the depthwise position information of the at least two reflection surfaces being obtained from calibration interference light generated by combining calibration measurement light and the first reference light generated in the first reference optical system, the calibration measurement light being generated by irradiating the calibration tool from the measurement optical system with the light from the light source. According to this configuration, the actual depthwise length of the subject eye can be calculated with high accuracy.

(Fourth aspect) In the third aspect of the first ophthalmic device disclosed herein, the specific time and a time at which the calibration interference light is measured by using the calibration tool to obtain the conversion formula may be substantially simultaneous According to this configuration, since the time when the specific-time reference position is measured and the time when the measurement is performed to obtain the conversion formula are substantially simultaneous, accuracy of the measurement of the subject eye can be improved.

(Fifth aspect) In the first ophthalmic device disclosed herein, the first ophthalmic device may further comprise a storage unit configured to store a specific-time reference position indicating the reference position adjusted at a specific time, the specific-time reference position being a position calculated from the reference interference light generated by combining the second reference light generated in the second reference optical system and the first reference light generated in the first reference optical system at the specific time. The first reference optical system may comprise an adjuster configured to adjust an optical path length of the first reference light, and the controller may be configured to calculate a measurement-time reference position that is the reference position calculated based on the reference interference signal outputted from the detector when the subject eye is measured and to control the adjuster so that the measurement-time reference position calculated when the subject eye is measured matches the specific-time reference position stored in the storage unit. According to this configuration, the subject eye can be measured in substantially the same state as the state at the specific time by adjusting the optical path length of the first reference light.

(Sixth aspect) In the fifth aspect of the first ophthalmic device disclosed herein, the storage unit may be configured to further store a conversion formula for converting the depthwise position information of the subject eye calculated based on the measurement interference signal to an actual measurement of the subject eye, the controller may be configured to further calculate the actual measurement of the subject eye by converting the depthwise position information of the subject eye calculated based on the measurement interference signal with the conversion formula, and the conversion formula may be obtained by using (A) depthwise position information of at least two reflection surfaces of a calibration tool having a known optical path length difference and (B) the optical path length difference between the at least two reflection surfaces, the depthwise position information of the at least two reflection surfaces being obtained from calibration interference light generated by combining calibration measurement light and the first reference light generated in the first reference optical system, the calibration measurement light being generated by irradiating the calibration tool from the measurement optical system with the light from the light source. According to this configuration, the actual depthwise length of the subject eye can be calculated with high accuracy.

(Seventh aspect) In the sixth aspect of the first ophthalmic device disclosed herein, the specific time and a time at which the calibration interference light is measured by using the calibration tool to obtain the conversion formula may be substantially simultaneous. According to this configuration, since the specific time and the time at which the measurement is performed to obtain the conversion formula are substantially simultaneous, the accuracy of the measurement of the subject eye can be improved.

(Eighth aspect) In any of the fifth to seventh aspects of the first ophthalmic device disclosed herein, the controller may be configured to: detect the reference interference light with the detector while the switching unit is in the second state; control the adjuster so that the measurement-time reference position calculated based on the reference interference signal outputted from the detector matches the specific-time reference position stored in the storage unit; and detect the measurement interference light while the switching unit is in the first state after the optical path length of the first reference light is adjusted by the adjuster. According to this configuration, the subject eye is measured after the optical path length of the first reference light is adjusted to be in the same state as the specific time. Due to this, the subject eye can be measured under the same conditions as those of the specific time (such as pre-shipping calibration or repair calibration).

A second ophthalmic device disclosed herein may comprise: a first OCT configured to measure a first depthwise position of a first part of a subject eye; a second OCT configured to measure a second depthwise position of a second part of the subject eye, the second part being different from the first part; and a controller configured to calculate a depthwise length from the first part to the second part based on the first depthwise position measured by the first OCT and the second depthwise position measured by the second OCT. The first OCT may comprise: a first light source; a first measurement optical system configured to generate first measurement light by irradiating the first part of the subject eye with light from the first light source; a first reference optical system configured to generate first reference light by using the light from the first light source; a second reference optical system configured to generate second reference light by using the light from the first light source, the second reference light being used for calculating a first reference position; a first interference optical system configured to generate first measurement interference light by combining the first measurement light and the first reference light and to generate first reference interference light by combining the second reference light and the first reference light; and a first detector configured to detect the first measurement interference light and output a first measurement interference signal and to detect the first reference interference light and output a first reference interference signal. The second reference optical system may include an optical path branching from the first measurement optical system, the first measurement optical system my comprise a first switching unit configured to switch between a first state and a second state, the first state being a state in which the subject eye is irradiated with the light from the first light source and the second state being a state in which the light from the first light source is guided to the second reference optical system, and when the subject eye is measured, the first detector may be configured to detect the first measurement interference light while the first switching unit is in the first state, and to detect the first reference interference light while the first switching unit is in the second state.

With the above ophthalmic device as well, the first measurement interference light is detected while the first detector is in the first state and the first reference interference light is detected while the first detector is in the second state. Due to this, the first reference position calculated from the first reference interference signal can be set to a desired position irrelevant to the depthwise position information of the subject eye that is calculated from the first measurement interference signal.

(Ninth aspect) In the second ophthalmic device disclosed herein, the second OCT may comprise: a second light source; a second measurement optical system configured to generate second measurement light by irradiating the second part of the subject eye with light from the second light source; a third reference optical system configured to generate third reference light by using the light from the second light source; a fourth reference optical system configured to generate fourth reference light by using the light from the second light source, the fourth reference light being used for calculating a second reference position; a second interference optical system configured to generate second measurement interference light by combining the second measurement light and the third reference light and to generate second reference interference light by combining the fourth reference light and the third reference light; and a second detector configured to detect the second measurement interference light and output a second measurement interference signal and to detect the second reference interference light and output a second reference interference signal. The fourth reference optical system may include an optical path branching from the second measurement optical system, the second measurement optical system may comprise a second switching unit configured to switch between a third state and a fourth state, the third state being a state in which the subject eye is irradiated with the light from the second light source and the fourth state being a state in which the light from the second light source is guided to the fourth reference optical system, and when the subject eye is measured, the second detector may be configured to detect the second measurement interference light while the second switching unit is in the third state, and to detect the second reference interference light while the second switching unit is in the fourth state. According to this configuration, similar to the first OCT, the second reference position can be set to a desired position with the second OCT.

(Tenth aspect) In the ninth aspect of the second ophthalmic device disclosed herein, when the first switching unit is switched to the first state, the second switching unit may be switched to the third state, when the first switching unit is switched to the second state, the second switching unit may be switched to the fourth state, and the first switching unit and the second switching unit may be a single switching unit shared by the first measurement optical system and the second measurement optical system. According to this configuration, since the first switching unit and the second switching unit are a single switching unit shared by the first measurement optical system and the second measurement optical system, the configuration of the optical system can be simplified and the switch performed by each of the switching unit can be facilitated.

(Eleventh aspect) In the ninth or tenth aspect of the second ophthalmic device disclosed herein, the ophthalmic device may further comprise a storage unit configured to store a depthwise distance between a measurement area of the first OCT and a measurement area of the second OCT adjusted at a specific time, a first specific-time reference position indicating the first reference position adjusted at the specific time, and a second specific-time reference position indicating the second reference position adjusted at the specific time. The controller may be configured to calculate the depthwise length from the first part to the second part based on: (1) a difference between a first measurement-time reference position and the first specific-time reference position stored in the storage unit, the first measurement-time reference position being calculated based on the first reference interference signal outputted from the first detector when the subject eye is measured; (2) the first position of the subject eye calculated based on the first measurement interference signal outputted from the first detector when the subject eye is measured; (3) a difference between a second measurement-time reference position and the second specific-time reference position stored in the storage unit, the second measurement-time reference position being calculated based on the second reference interference signal outputted from the second detector when the subject eye is measured; (4) the second position of the subject eye calculated based on the second measurement interference signal outputted from the second detector when the subject eye is measured; and (5) the depthwise distance between the measurement area of the first OCT and the measurement area of the second OCT stored in the storage unit. According to this configuration, the depthwise length between the first part and the second part can be calculated with high accuracy.

(Twelfth aspect) In the eleventh aspect of the second ophthalmic device disclosed herein, the storage unit may be configured to further store: a first conversion formula for converting depthwise position information of the subject eye calculated based on the first measurement interference signal to an actual measurement of the subject eye in the measurement area of the first OCT; and a second conversion formula for converting depthwise position information of the subject eye calculated based on the second measurement interference signal to an actual measurement of the subject eye in the measurement area of the second OCT. The controller may be configured to further calculate the actual measurement of the subject eye in the measurement area of the first OCT by converting the depthwise position information of the subject eye calculated based on the first measurement interference signal with the first conversion formula, and to further calculate the actual measurement of the subject eye in the measurement area of the second OCT by converting the depthwise position information of the subject eye calculated based on the second measurement interference signal with the second conversion formula. The first conversion formula may be obtained by using (A1) depthwise position information of at least two reflected surfaces of a first calibration tool having a known an optical path length difference and (B1) the optical path length difference between the at least two reflected surfaces, the depthwise position information of the at least two reflected surfaces of the first calibration tool is obtained from first calibration interference light generated by combining first calibration measurement light and first reference light generated in the first reference optical system, the first calibration measurement light being generated by irradiating the first calibration tool from the first measurement optical system with the light from the first light source. The second conversion formula may be obtained by using (A2) depthwise position information of at least two reflected surfaces of a second calibration tool having a known optical path length difference and (B2) the optical path length difference between the at least two reflected surfaces, the depthwise position information of the at least two reflected surfaces of the second calibration tool is obtained from second calibration interference light generated by combining second calibration measurement light and third reference light generated in the third reference optical system, the second calibration measurement light is generated by irradiating the second calibration tool from the second measurement optical system with the light from the second light source. According to this configuration, the actual depthwise length of the subject eye can be calculated with high accuracy.

(Thirteenth aspect) In the twelfth aspect of the second ophthalmic device disclosed herein, the first specific-time reference position may be a position calculated from the first reference interference light generated by combining the second reference light generated in the second reference optical system and the first reference light generated in the first reference optical system at the specific time. The second specific-time reference position may be a position calculated from the second reference interference light generated by combining the fourth reference light generated in the fourth reference optical system and the third reference light generated in the third reference optical system at the specific time. The specific time, a time at which the first calibration tool is irradiated with the first measurement light to obtain the first conversion formula and a time at which the second calibration tool is irradiated to the second measurement light to obtain the second conversion formula may be substantially simultaneous. According to this configuration, since the specific time and the time at which the measurement is performed to obtain the conversion formula are substantially simultaneous, the accuracy of the measurement of the subject eye can be improved.

(Fourteenth aspect) In the ninth or tenth aspect of the second ophthalmic device disclosed herein, the ophthalmic device may further comprise an adjuster disposed on at least one of the first reference optical system and the third reference optical system and configured to adjust an optical path length of the at least one of the first reference optical system and the third reference optical system. The controller may be configured to control the adjuster so that a distance between a first measurement-time reference position calculated from the first reference interference signal when the subject eye is measured and a second measurement-time reference position calculated from the second reference interference signal when the subject eye is measured matches a predetermined distance. According to this configuration, the subject eye is measured after the relationship of the optical path lengths of the first and third reference optical systems is adjusted to the predetermined distance. Due to this, the depthwise length between the first part and the second part of the subject eye can be calculated with high accuracy.

(Fifteenth aspect) in the fourteenth aspect of the second ophthalmic device disclosed herein, the predetermined distance may be a distance between a first specific-time reference position calculated from the first reference interference signal at a specific time and a second specific-time reference position calculated from the second reference interference signal at the specific time. According to this configuration, the subject eye can be measured under the same conditions as those of the specific time (such as pre-shipping calibration or repair calibration).

(Sixteenth aspect) In the fourteenth or fifteenth aspect of the second ophthalmic device disclosed herein, the controller may be configured to: detect the first reference interference light with the first detector while the first switching unit is in the second state; detect the second reference interference light with the second detector while the second switching unit is the fourth state; control the adjuster so that a difference between the first measurement-time reference position calculated based on the first reference interference signal outputted from the first detector and the second measurement-time reference position calculated based on the second reference interference signal outputted from the second detector matches the predetermined distance, and after the optical path length is adjusted by the adjuster, detect the first measurement interference signal while the first switching unit is in the first state, and detect the second measurement interference signal while the second switching unit is in the third state.

EMBODIMENTS

First Embodiment

An ophthalmic device 10 according to a first embodiment will be described. The ophthalmic device 10 comprises an anterior part OCT (an example of "first OCT") configured to capture tomographic images of an anterior part of a subject eye (example of "first part") and a retina OCT (an example of "second OCT") configured to capture tomographic images of a retina of the subject eye (an example of "second part"). The ophthalmic device 10 enables to obtain a clear tomographic image of each of the anterior part and the retina by capturing the tomographic images using different OCTs for the anterior part and the retina.

Figure 2:
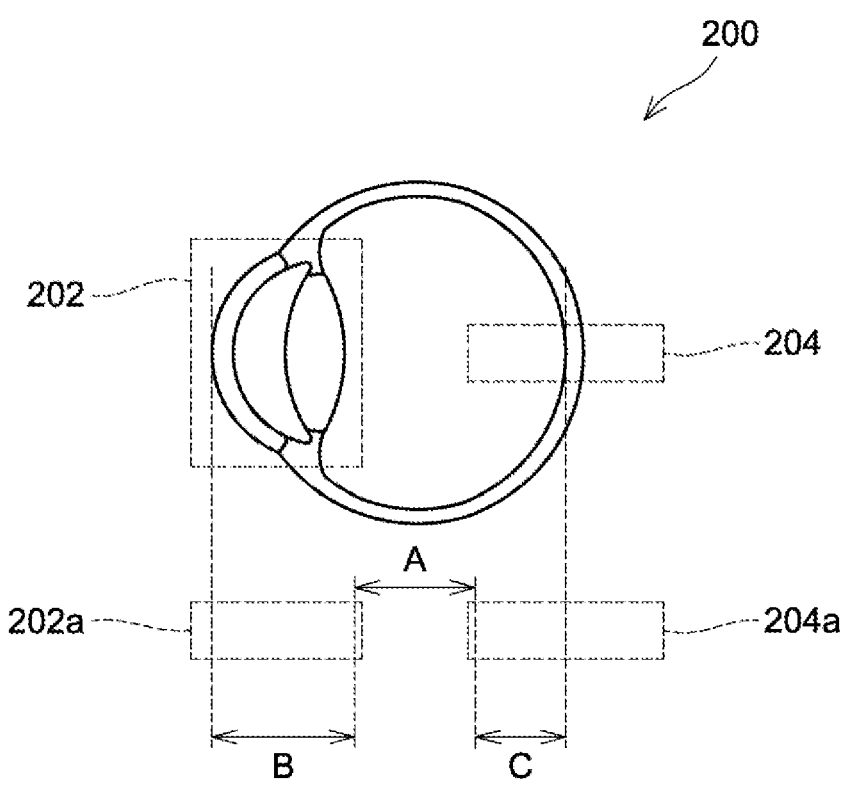
FIG. 2 shows a relationship of measurement areas of a subject eye measured by two OCTs of the ophthalmic device according to the first embodiment.

That is, as shown in FIG. 2, the ophthalmic device 10 captures a tomographic image of an anterior part 202 of a subject eye 200 using the anterior part OCT and a tomographic image of a retina 204 using the retina OCT. In order to clearly capture each of the anterior part 202 and the retina 204, an imaging range 202a (depthwise length B) of the anterior part OCT and an imaging range 204a (depthwise length C) of the retina OCT are set so that they do not overlap. Due to this, when an axial length (length from a corneal surface of the anterior part 202 (an example of "first position") to a retinal surface of the retina 204 (an example of "second position")) is to be measured, for example, a depthwise positional relationship between the imaging range 202a of the anterior part OCT and the imaging range 204a of the retina OCT needs to be identified in advance. For example, a distance (length A) from a rearmost position in the imaging range 202a of the anterior part OCT to a frontmost position of the imaging range 204a of the retina OCT is required. Thus, the configuration of the optical systems of the ophthalmic device 10 is designed and calibration of the optical systems of the ophthalmic device 10 is performed when the ophthalmic device 10 is shipped so that the depthwise positional relationship between the imaging range 202a of the anterior part OCT and the imaging range 204a of the retina OCT satisfies a predetermined positional relationship. However, the optical systems of the ophthalmic device 10 undergo changes such as post-shipment chronological changes and those caused by environment (such as temperature) upon the measurement, thus measurement under the condition calibrated in a calibration process cannot be achieved. Due to this, the ophthalmic device 10 is configured to calculate the axial length by correcting change(s) in optical path lengths of the optical systems.

Firstly, the configuration of the optical systems of the ophthalmic device 10 will be described. As shown in FIG. 1, the ophthalmic device 10 includes the anterior part OCT (12, 18a to 18e, 20, 22, 26, 24, 28, 34, 36, 38, 40, 43) and the retina OCT (14, 16, 30a to 30d, 32, 33, 36, 38, 41, 42).

The anterior part OCT is a Fourier domain optical coherence tomographic device (so-called SS-OCT) comprising a wavelength sweeping light source 12 (an example of "first light source"), an anterior part measurement optical system (an example of "first measurement optical system"), a first anterior part reference optical system (an example of "first reference optical system"), a second anterior part reference optical system (an example of "second reference optical system"), an anterior part interference optical system (an example of "first interference optical system"), and an anterior part detector 28 (an example of "first detector").

The anterior part measurement optical system comprises optical fibers 18a, 18b, 18d, a coupler 20, a circulator 22, a lens 34, and a Galvano scanner 36. Light emitted from the light source 12 is inputted to the coupler 20 through the optical fiber 18a. The coupler 20 is configured to split the light from the light source 12 into measurement light and first reference light. The measurement light (an example of "first measurement light") split by the coupler 20 is outputted to the optical fiber 18b. The circulator 22 is arranged on the optical fiber 18b. The measurement light outputted to the optical fiber 18b travels through the circulator 22 and is outputted toward the lens 34 from the end of the optical fiber 18b. The measurement light outputted to the lens 34 is further outputted to the 2-axis Galvano scanner 36. The Galvano scanner 36 is configured to be tilted by a driving device that is not shown, and a position at which the measurement light is emitted to the subject eye 200 is scanned by tilting the Galvano scanner 36. Reflected light from the subject eye 200 is inputted to the lens 34 via the Galvano scanner 36 in a reversed direction from the aforementioned direction. The reflected light inputted to the lens 34 travels through the optical fiber 18b and is inputted to the circulator 22. The reflected light inputted to the circulator 22 travels through the optical fiber 18d and is inputted to a coupler 26. In FIG. 1, the configuration of the optical systems has been simplified, thus the optical fiber 18b is depicted as if it is penetrating through a lens 33, however, the optical fiber 18b actually does not penetrate through the lens 33. Further, in FIG. 1, the circulator 22 is depicted as if it is arranged on an optical fiber 30c to be described later, however, the circulator 22 is actually not arranged on the optical fiber 30c.

The first anterior part reference optical system comprises optical fibers 18a, 18c, 18e, the coupler 20, a circulator 24, a lens 43, and a reference mirror 40. As aforementioned, the light emitted from the light source 12 is inputted to the coupler 20 through the optical fiber 18a, and is split into the measurement light and the first reference light in the coupler 20. The first reference light outputted from the coupler 20 (an example of "first reference light") is inputted to the optical fiber 18c, travels through the circulator 24, and is outputted toward the lens 43 from the end of the optical fiber 18c. The first reference light outputted to the lens 43 is reflected on the reference mirror 40, and is then inputted again into the lens 43. The reflected light inputted to the lens 43 travels through the optical fiber 18c and is inputted to the circulator 24. The reflected light inputted to the circulator 24 is inputted to the coupler 26 through the optical fiber 18e.

The second anterior part reference optical system comprises an optical path that branches from the anterior part measurement optical system and comprises a reference mirror 38 arranged on this optical path. The aforementioned Galvano scanner 36 is tilted by the driving device that is not shown, by which it switches between a first state in which the light from the light source 12 is emitted to the subject eye 200 and a second state in which the light from the light source 12 is emitted to the reference mirror 38. The Galvano scanner 36 functions as a "first switching unit" configured to switch between the first state and the second state. Further, in the present embodiment, in the state where the light from the light source 12 is emitted onto the subject eye 200, the light from the light source 12 is not guided to the reference mirror 38. On the other hand, in the state where the light from the light source 12 is guided to the reference mirror 38, the light from the light source 12 is not emitted onto the subject eye 200. That is, an entirety of the light guided from the light source 12 to the anterior part measurement optical system is emitted to the subject eye 200 or to the reference mirror 38. The light emitted to the reference mirror 38 (an example of "second reference light") is reflected on the reference mirror 38 and is inputted to the circulator 22 through the Galvano scanner 36, the lens 34, and the optical fiber 18b. The light inputted to the circulator 22 is inputted to the coupler 26 through the optical fiber 18d.

The anterior part interference optical system comprises the coupler 26. The coupler 26 is configured to combine the light reflected from the subject eye 200 (first measurement light) and the light reflected from the reference mirror 40 (first reference light) and generate interference light (an example of "first measurement interference light"), and to combine the light reflected from the reference mirror 38 (second reference light) and the light reflected from the reference mirror 40 (first reference light) and generate interference light (an example of "first reference interference light"). The interference light generated in the coupler 26 is inputted to the anterior part detector 28. The anterior part detector 28 is a balance detector and is configured to detect the interference light inputted from the coupler 26 and output an interference signal (electric signal). The interference signal outputted from the anterior part detector 28 is inputted to a controller 44 (shown in FIG. 3) described later.

The retina OCT is a spectrum domain optical coherence tomographic device (so-called SD-OCT) comprising a wideband wavelength light source 14 (an example of "second light source"), and comprises a retina measurement optical system (an example of"second measurement optical system"), a first retina reference optical system (an example of "third reference optical system"), a second retina reference optical system (an example of "fourth reference optical system"), a retina interference optical system (an example of"second interference optical system"), and a retina detector 16 (an example of "second detector").

The retina measurement optical system comprises optical fibers 30*a*, 30*c*, a coupler 32, the lens 33, and the Galvano scanner 36. Light outputted from the light source 14 is inputted to the coupler 32 through the optical fiber 30*a*. The coupler 32 is configured to split the light from the light source 14 into measurement light (an example of "second measurement light") and third reference light. The measurement light split by the coupler 32 is outputted to the optical fiber 30*c* and is outputted toward the lens 33 from the end of the optical fiber 30*c*. Similar to the anterior part OCT described above, the measurement light outputted to the lens 33 is outputted to the 2-axis Galvano scanner 36. The Galvano scanner 36 is driven by the driving device that is not shown, and a position at which the measurement light is emitted to the subject eye 200 is scanned. Reflected light from the subject eye 200 is inputted to the coupler 32 through the Galvano scanner 36, the lens 33, and the optical fiber 30*c* in a reversed direction from the aforementioned direction.

As it is apparent from the foregoing description, the optical path from the Galvano scanner 36 to the subject eye 200 is shared by the retina measurement optical system and the anterior part measurement optical system, and the Galvano scanner 36 is shared by the retina measurement optical system and the anterior part measurement optical system. In FIG. 1, the measurement light outputted from the end of the optical fiber 30*c* toward the lens 33 is depicted as if it penetrates through the lens 34, however, it actually does not penetrate through the lens 34. Further, as shown in FIG. 1, an optical path length from the end of the optical fiber 30*c* to the subject eye 200 in the retina measurement optical system is longer than an optical path length from the end of the optical fiber 18*b* to the subject eye 200 in the anterior part measurement optical system. That is, a portion between positions corresponding to the end of the optical fiber 30*c* and the end of the optical fiber 18*b* is configured by a bulk optical system in the retina measurement optical system, whereas the portion is configured with the optical fiber 18*b* in the anterior part measurement optical system. Due to this, a change in the optical path length of the anterior part measurement optical system and a change in the optical path length of the retina measurement optical system caused by a temperature change do not become identical to one another. Further, since a temperature in the ophthalmic device 10 is not uniform, a temperature of each of the optical systems does not become uniform over its entire optical path length. Due to these factors as well, the changes in the optical path lengths of the respective optical systems caused by a temperature are nonuniform.

The first retina reference optical system comprises optical fibers 30*a*, 30*b*, the coupler 32, a lens 41, and a reference mirror 42. As described above, the light emitted from the light source 14 is inputted to the coupler 32 through the optical fiber 30*a* and is split in the coupler 32 into measurement light and third reference light. The reference light outputted from the coupler 32 (an example of "third reference light") travels through the optical fiber 30*b* and is outputted from the end of the optical fiber 30*b* toward the lens 41. The third reference light outputted to the lens 41 is reflected on the reference mirror 42, and is inputted to the coupler 32 through the lens 41 and the optical fiber 30*b*.

The second retina reference optical system comprises an optical path that branches from the retina measurement optical system, and comprises the reference mirror 38 arranged on this optical path. As it is apparent from FIG. 1, the reference mirror 38 is shared by the second retina reference optical system and the second anterior part reference optical system, and the second retina reference optical system has identical configuration as the second anterior part reference optical system. Thus, the Galvano scanner 36 is driven to switch between a third state in which the light from the light source 14 is emitted to the subject eye 200 and a fourth state in which the light from the light source 14 is emitted to the reference mirror 38. That is, the Galvano scanner 36 functions as a "second switching unit" configured to switch between the third state and the fourth state. As it will be described later, since the anterior part OCT and the retina OCT capture the tomographic images of the subject eye 200 simultaneously, the retina OCT is switched to the third state when the Galvano scanner 36 switches the anterior part OCT to the first state. Further, when the Galvano scanner 36 switches the anterior part OCT to the second state, the retina OCT is switched to the fourth state. In the retina OCT as well, an entirety of the light guided from the light source 14 to the retina measurement optical system is emitted to the subject eye 200 or to the reference mirror 38. The light emitted to the reference mirror 38 (an example of"fourth reference light") is reflected on the reference mirror 38 and is inputted to the coupler 32 through the Galvano scanner 36 and the optical fiber 30*c*.

The retina interference optical system comprises the coupler 32. The coupler 32 is configured to combine the light reflected from the subject eye 200 (second measurement light) and the light reflected from the reference mirror 42 (third reference light) and generate interference light (an example of "second measurement interference light"), and to combine the light reflected from the reference mirror 38 (fourth reference light) and the light reflected from the reference mirror 42 (third reference light) and generate interference light (an example of "second reference interference light"). The interference light generated in the coupler 32 is inputted to the retina detector 16. The retina detector 16 is a splitter and is configured to split and detect the inputted interference light and output an interference signal (electric signal). The interference signal outputted from the retina detector 16 (spectrum information of the interference light) is inputted to the controller 44 (shown in FIG. 3) described later.

Figure 3:
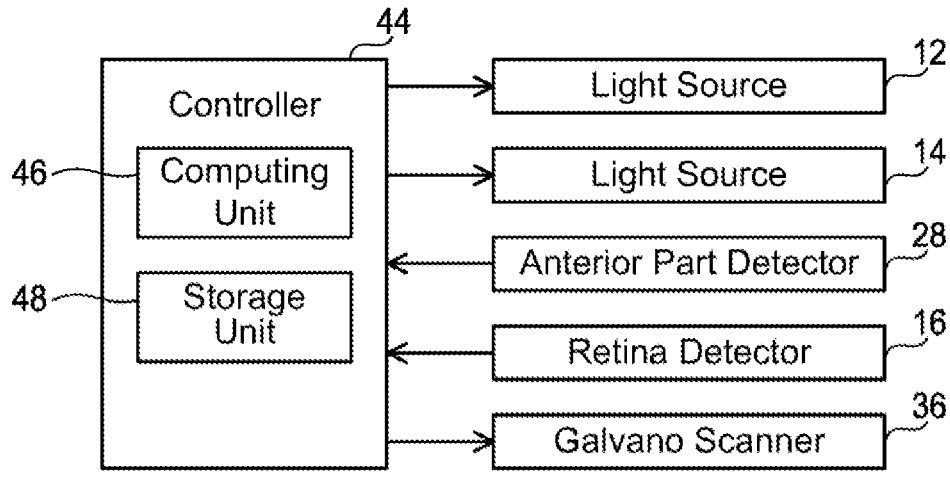
FIG. 3 is a block diagram showing a configuration of a control system of the ophthalmic device according to the first embodiment.

Next, the controlling configuration of the ophthalmic device 10 will be described. As shown in FIG. 3, the ophthalmic device 10 is controlled by the controller 44. The controller 44 is configured of a microcomputer (microprocessor) configured of, for example, a CPU, a ROM, and a RAM, and functions as a computing unit 46 configured to calculate the axial length of the subject eye 200 and a storage unit 48 configured to store various types of information. The controller 44 has the light sources 12, 14, the anterior part detector 28, the retina detector 16, and the Galvano scanner 36 connected thereto. The controller 44 is configured to control on/off of the light sources 12, 14 and drive the Galvano scanner 36. Further, the controller 44 is configured to generate tomographic images of the anterior part 202 of the subject eye 200 using the interference signals inputted from the anterior part detector 28 and generate tomographic images of the retina 204 of the subject eye 200 using the interference signals inputted from the retina detector 16. The tomographic images generated by the controller 44 are displayed on a monitor that is not shown.

Further, the computing unit 46 of the controller 44 is configured to calculate the axial length of the subject eye 200 (length from the anterior surface of the cornea to the retinal surface of the subject eye 200) based on the interference signal inputted from the anterior part detector 28 (depthwise position information of the anterior part 202a) and the interference signal inputted from the retina detector 16 (depthwise position information of the retina 204). As aforementioned, in order to calculate the axial length of the subject eye 200, the depthwise positional relationship between the imaging range 202a of the anterior part OCT and the imaging range 204a of the retina OCT (such as the distance (length A) from the rearmost position in the imaging range 202a of the anterior part OCT to the frontmost position of the imaging range 204a of the retina OCT) is required. Thus, the storage unit 48 of the controller 44 stores the depthwise positional relationship (length A) of the imaging range 202a of the anterior part OCT and the imaging range 204a of the retina OCT at the time of shipping of the ophthalmic device 10. More specifically, a conversion formula (an example of "first conversion formula") for converting the depthwise position information of the subject eye 200 calculated from the interference signals measured by the anterior part OCT to an actual measurement of the subject eye and a conversion formula (an example of "second conversion formula") for converting the depthwise position information of the subject eye 200 calculated form the interference signals measured by the retina OCT to the actual measurement of the subject eye are stored, and further, the depthwise positional relationship of the imaging range 202a of the anterior part OCT and the imaging range 204a of the retina OCT (such as the length A) at the time of shipment of the ophthalmic device 10 is stored. These conversion formulas and the positional relationships are obtained upon performing the calibration process of the optical systems that is performed at the time of shipment of the ophthalmic device 10.

Even if the optical systems of the ophthalmic device 10 are calibrated upon the shipping and the depthwise positional relationship (conversion formula (length A)) of the imaging range 202a and the imaging range 204a at the time of shipping is stored, the optical path lengths of the optical systems change by post-shipping chronological changes and the environment (such as temperature) at the time of measurement. As a result, the depthwise positional relationship of the imaging range 202a and the imaging range 204a changes, and with the depthwise positional relationship changed, the axial length cannot be calculated correctly. Thus, in the present embodiment, the storage unit 48 of the controller 44 further stores a position of the reference mirror 38 in the anterior part OCT at the time of shipping (an example of "first specific-time reference position") and a position of the reference mirror 38 in the retina OCT at the time of shipping (an example of "second specific-time reference position").

Here, examples of the calibration process of the optical systems performed at the time of shipment of the ophthalmic device 10 and a process for obtaining the conversion formulas for calculating the axial length will be described. When the calibration process of the optical systems is to be performed, a calibration tool (glass block) having at least two reflection surfaces having a known optical path length difference is used. That is, front and rear surfaces of the glass block serve as reflection surfaces, and a length from the front surface to the rear surface (thickness of the glass block) is known. Due to this, the glass block can be used as the calibration tool.

As specific processes, the calibration tool (glass block) is positioned at the position of the anterior part of the subject eye 200, the calibration tool is measured by the anterior part OCT, and the position of the front surface and the position of the rear surface of the calibration tool are obtained. As aforementioned, since the optical path length difference between the position of the front surface and the position of the rear surface of the calibration tool is known, the conversion formula (first conversion formula) for converting the value measured by the anterior part OCT to the actual length is thereby obtained. Similarly, the calibration tool (glass block) is positioned at the position of the retina of the subject eye 200, the calibration tool is measured by the retina OCT, and the position of the front surface and the position of the rear surface of the calibration tool are obtained. Due to this, the conversion formula (second conversion formula) for converting the value measured by the retina OCT to the actual length is thereby obtained. Then, the calibration tool is arranged so that the front surface of the calibration tool is positioned in the imaging range 202a of the anterior part OCT and the rear surface of the calibration tool is positioned in the imaging range 204a of the retina OCT, the position of the front surface of the calibration tool is obtained by the anterior part OCT, and the position of the rear surface of the calibration tool is obtained by the retina OCT. Due to this, the positional relationship (such as the length A) of the imaging range 202a of the anterior part OCT and the imaging range 204a of the retina OCT can be obtained. The conversion formulas for calculating the axial length of the subject eye 200 (actual length thereof) are obtained by these measurements, and the obtained conversion formulas are stored in the storage unit 48.

At the same time as obtaining the aforementioned conversion formulas, the position of the reference mirror 38 in the anterior part OCT and the position of the reference mirror 38 in the retina OCT are measured. That is, upon measuring the calibration tool using the anterior part OCT, the Galvano scanner 36 is driven after this measurement is completed and the light from the light source 12 is emitted to the reference mirror 38. Then, the position of the reference mirror 38 in the anterior part OCT is obtained from reference interference light obtained by combing the second reference light reflected on the reference mirror 38 and the first reference light. Similarly, upon measuring the calibration tool using the retina OCT, the Galvano scanner 36 is driven after this measurement is completed and the light from the light source 14 is emitted to the reference mirror 38. Then, the position of the reference mirror 38 in the retina OCT is obtained from reference interference light obtained by combing the fourth reference light reflected on the reference mirror 38 and the third reference light. Then, these two reference positions are stored in the storage unit 48. By storing the conversion formulas and the reference positions in the storage unit 48, the calibration process at the time of shipment of the ophthalmic device 10 is completed. The calibration process as above may be performed not only at the time of shipment of the ophthalmic device 10 but at various other timings. For example, it may be performed at the time of repairing or maintenance of the ophthalmic device 10. Further, in the above example, the process to measure the reference positions was performed after the measurement for obtaining the conversion formulas was performed, however, the measurement process for obtaining the conversion formulas may be performed after the process to measure the reference positions was performed.

Figure 4:
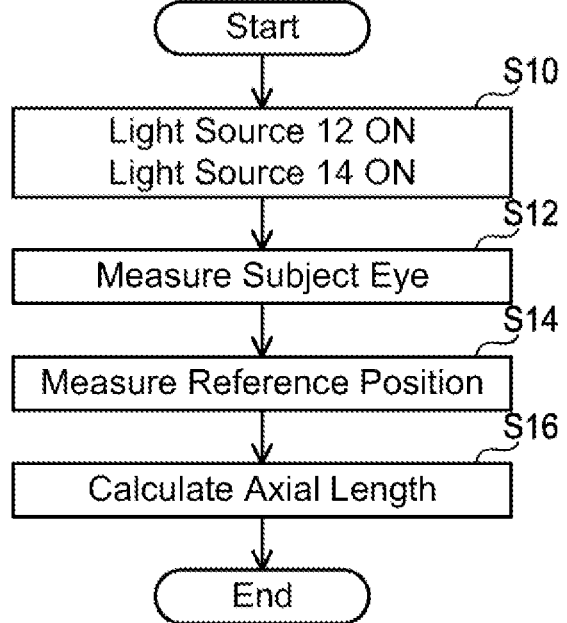
FIG. 4 is a flowchart showing a procedure for measuring an axial length of the subject eye using the ophthalmic device according to the first embodiment.

Next, the operation of the ophthalmic device 10 for measuring the axial length of the subject eye 200 after the shipment will be described. In order to measure the axial length of the subject eye 200, firstly the optical systems of the anterior part OCT and the retina OCT are positioned (aligned) relative to the subject eye 200. Then, the controller 44 turns on the light sources 12, 14 as shown in FIG. 4 (S10). By doing so, the light is outputted from each of the light sources 12, 14, and the outputted light is emitted onto the subject eye 200. That is, the light outputted from both the light sources 12, 14 is emitted simultaneously to the subject eye 200.

Then, the controller 44 captures tomographic images of the anterior part 202 and the retina 204 of the subject eye 200 (S12). Specifically, the controller 44 drives the Galvano scanner 36 and scans the light from the light sources 12, 14 to the measurement areas of the subject eye 200. Due to this, the interference light obtained from the light reflected on the anterior part 202 of the subject eye 200 is detected by the anterior part detector 28, and at the same time the interference light obtained from the light reflected on the retina 204 of the subject eye 200 is detected by the retina detector 16. Due to this, the controller 44 generates the tomographic image of the anterior part 202 of the subject eye 200 based on the interference signal inputted from the anterior part detector 28 and generates the tomographic image of the retina 204 of the subject eye 200 based on the interference signal inputted from the retina detector 16.

Next, the controller 44 emits the light from the light sources 12, 14 to the reference mirror 38 and measures the position of the reference mirror 38 (S14). Specifically, the controller 44 drives the Galvano scanner 36 to guide the light from the light sources 12, 14 to the second reference optical system, and emits the light from the light sources 12, 14 to the reference mirror 38. As aforementioned, in the state of S14, the light from the light sources 12, 14 is not emitted to the subject eye 200. Due to this, the anterior part detector 28 detects only the interference light obtained from the light emitted to the reference mirror 38 (second reference light) and the first reference light, and the retina detector 16 detects only the interference light obtained from the light emitted to the reference mirror 38 (fourth reference light) and the third reference light. Based on the detected interference light as above, the controller 44 calculates the position of the reference mirror 38 in the anterior part OCT and the position of the reference mirror 38 in the retina OCT.

Next, the controller 44 calculates the axial length of the subject eye 200 based on the measurement result of the subject eye 200 as measured in S12 and the measurement result of the reference mirror 38 as measured in S14 (S16). That is, in S12, the tomographic image of the anterior part 202 of the subject eye 200 is captured by the anterior part OCT and the tomographic image of the retina 204 of the subject eye 200 is captured by the retina OCT. Thus, the controller 44 can identify the position of the corneal surface of the subject eye 200 from the tomographic image of the anterior part 202 and the position of the retinal surface of the subject eye 200 from the tomographic image of the retina 204. Here, the storage unit 48 of the controller 44 stores the positional relationship (length A) of the imaging range 202a of the anterior part OCT and the imaging range 204a of the retina OCT as well as the conversion formulas. Thus, if there is no change in the optical path lengths of the optical systems in the anterior part OCT and the retina OCT, the controller 44 can calculate the axial length from the identified positions of the corneal surface and the retinal surface, the conversion formulas (length A), and the positional relationship.

However, as already explained, the optical path lengths of the optical systems of the ophthalmic device 10 change due to the post-shipping chronological changes and the environment (such as temperature) at the time of measurement. Due to this, the controller 44 uses the position of the reference mirror 38 calculated in S14 to correct the position of the corneal surface and the position of the retinal surface identified from the tomographic images captured in S12. That is, the storage unit 48 of the controller 44 stores the position of the reference mirror 38 in the anterior part OCT at the time of shipping and the position of the reference mirror 38 in the retina OCT at the time of shipping. Thus, in each of the anterior part OCT and the retina OCT, a difference between the position of the reference mirror 38 measured in S14 and a position of the reference mirror 38 as stored in the storage unit 48 (that is, the change in the optical path length) is used to correct the positions of the corneal surface and the retinal surface identified from the tomographic images captured in S12. Next, the axial length is calculated from the corrected positions of the corneal surface and the retinal surface and the positional relationship (length A) of the imaging range 202a and the imaging range 204a. Due to this, the axial length of the subject eye 200 can be calculated with high accuracy. The axial length calculated in S16 is displayed in the monitor that is not shown.

In the ophthalmic device 10 of the first embodiment as described above, the anterior part OCT and the retina OCT each comprise the reference optical system, and the reference positions (position of the reference mirror 38) measured by the reference optical systems are used to correct the measurement results of the anterior part OCT and the retina OCT. Due to this, even if the optical path length of the optical system of the ophthalmic device 10 is changed over time or by temperature, the measurement results of the anterior part OCT and the retina OCT are corrected with consideration to the changes in the optical path lengths. Due to this, the axial length of the subject eye 200 can be calculated with high accuracy.

Further, the reference mirror 38 is irradiated with the light to measure the position of the reference mirror 38 (reference position) after the subject eye 200 is measured by emitting the light to the subject eye 200. That is, the measurement of the subject eye 200 and the measurement of the reference mirror 38 are not performed simultaneously. Due to this, the reference mirror 38 can be set to a desired position, and no issue arises even if position(s) of part(s) of the subject eye 200 (such as the cornea, crystalline lens, and retina) and the position of the reference mirror 38 are at the same position. Further, the measurement of the subject eye 200 and the measurement of the reference mirror 38 are not performed simultaneously, but the measurement of the reference mirror 38 is performed immediately after the measurement of the subject eye 200 is performed. Due to this, accuracy of calculation of the axial length is hardly affected. In the above example, the measurement of the reference mirror 38 is performed immediately after the measurement of the subject eye 200 is performed, however to the contrary, the measurement of the subject eye 200 may be performed immediately after the measurement of the reference mirror 38 is performed.

Second Embodiment

Next, an ophthalmic device 50 according to the second embodiment will be described. The ophthalmic device 50 according to the second embodiment comprises an anterior part OCT and a retina OCT, and each of these OCTs comprises a reference optical system for obtaining a reference position, and in this point, the ophthalmic device 50 is similar to the ophthalmic device 10 according to the first embodiment. However, the configuration of the reference optical systems of the ophthalmic device 50 according to the second embodiment is different, and the configuration for correcting the changes in the optical path lengths of the optical systems of the ophthalmic device 50 based on the reference positions obtained by the reference optical systems differs from that of the ophthalmic device 10 of the first embodiment. Hereinbelow, portions of the configuration of the ophthalmic device 50 of the second embodiment that are identical to that of the ophthalmic device 10 of the first embodiment will be explained briefly, and portions with different configurations from those of the first embodiment will be explained in detail.

Figure 5:
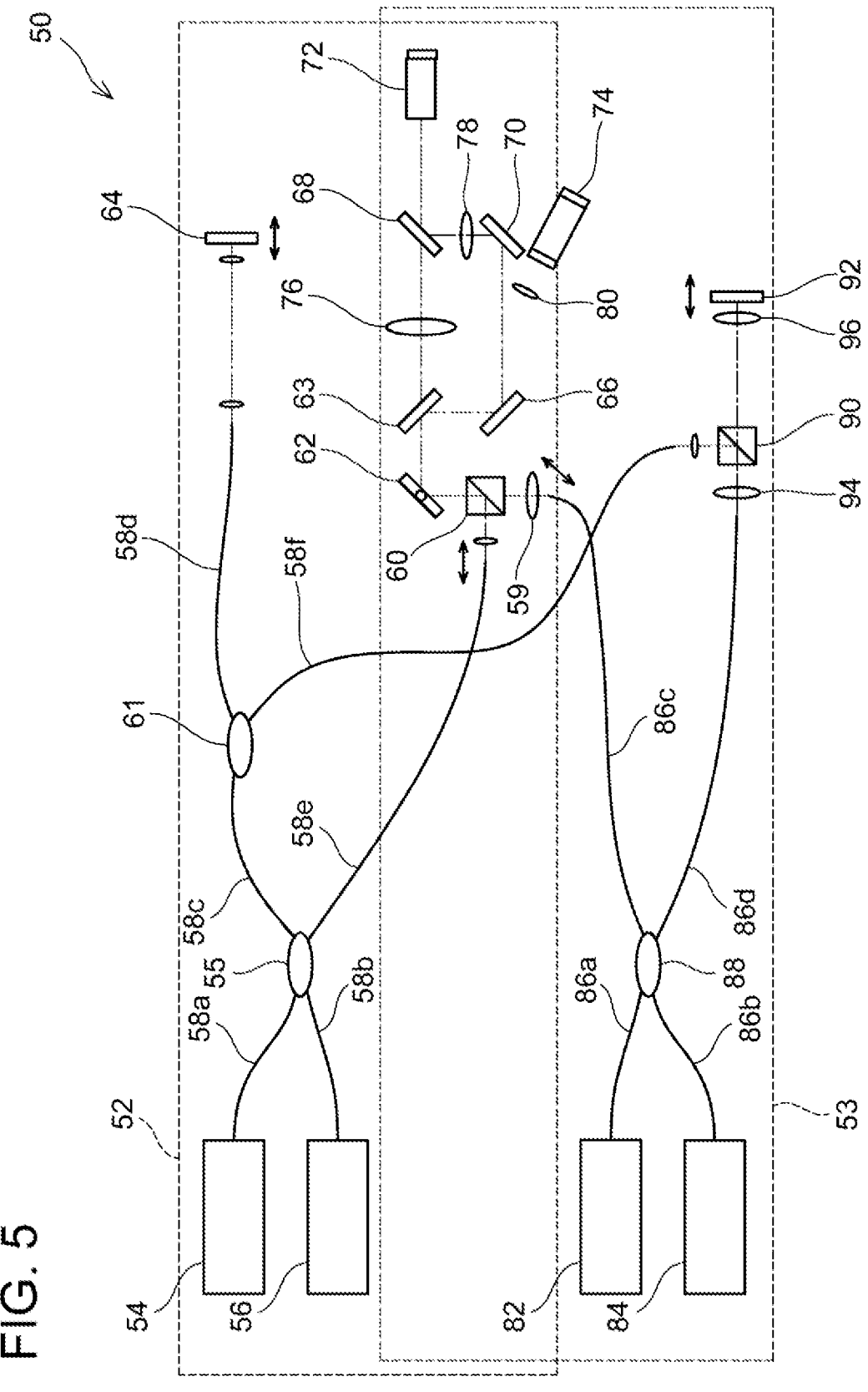
FIG. 5 shows a configuration of optical systems of an ophthalmic device according to a second embodiment.
Figure 6:
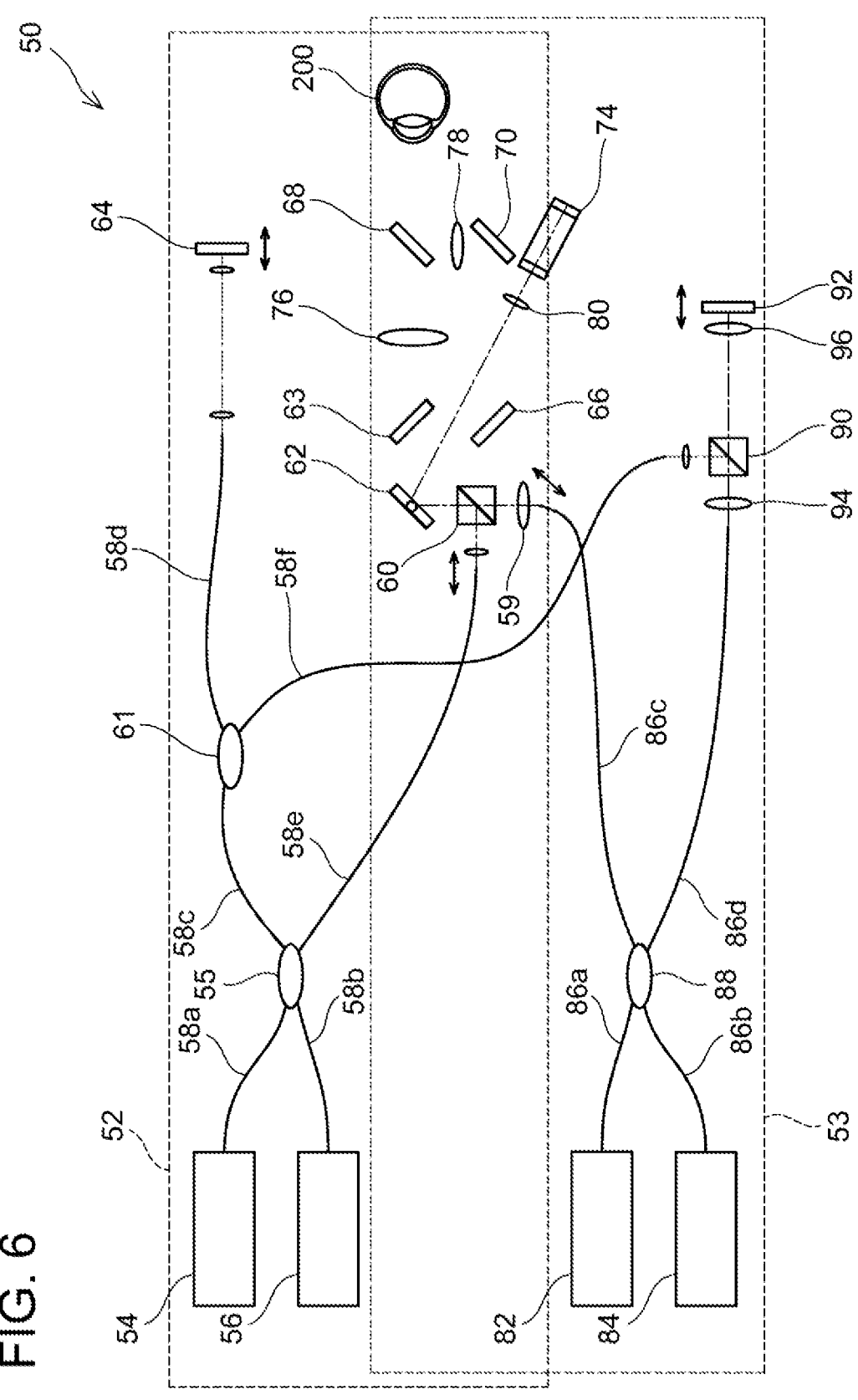
FIG. 6 shows the configuration of the optical systems of the ophthalmic device according to the second embodiment (at the time of optical system calibration).
Figure 7:
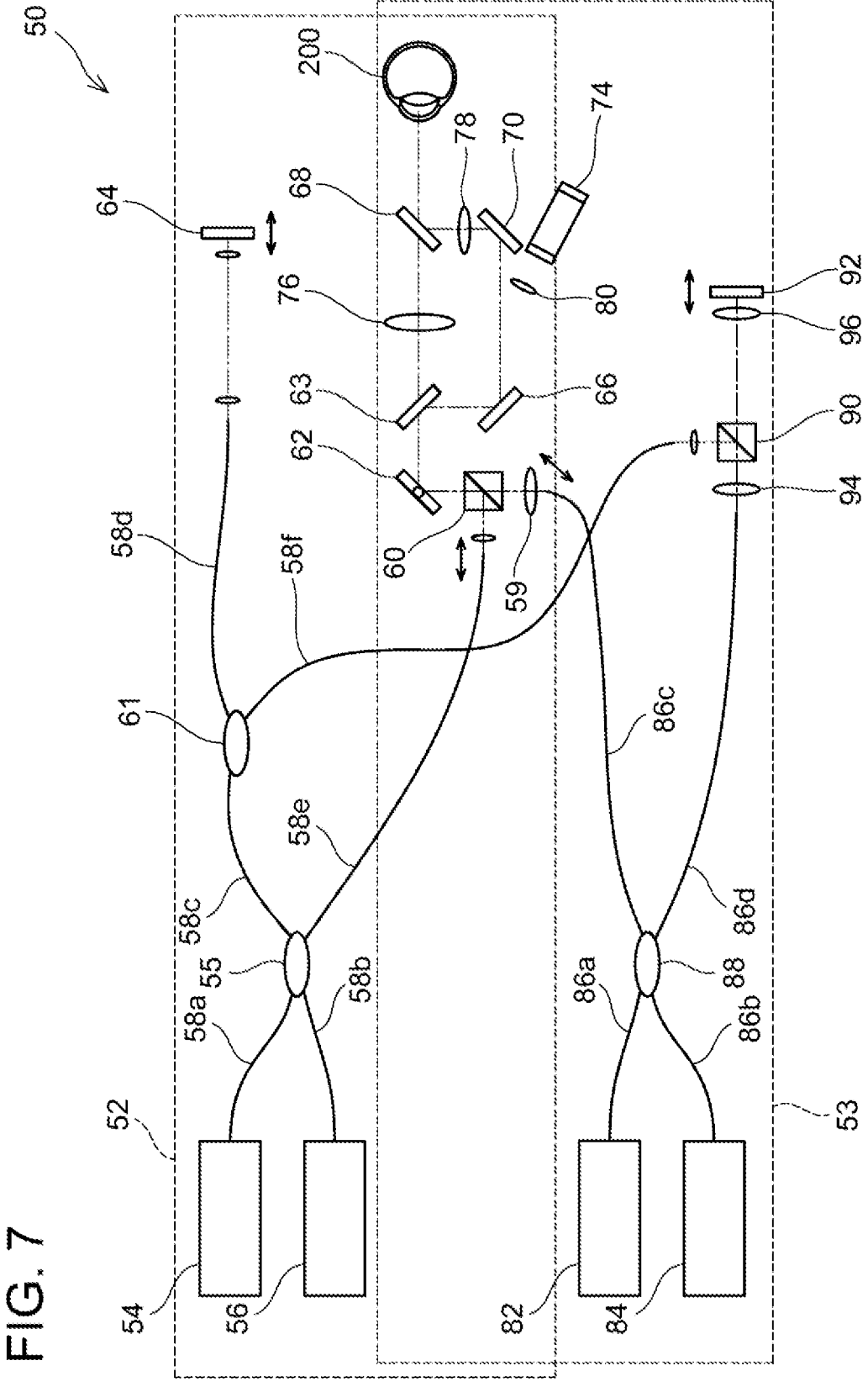
FIG. 7 shows the configuration of the optical systems of the ophthalmic device according to the second embodiment (at the time of subject eye measurement).

As shown in FIGS. 5 to 7, the ophthalmic device 10 comprises an anterior part OCT 53 (another example of "first OCT") configured to capture tomographic images of the anterior part of the subject eye and a retina OCT 52 (another example of "second OCT") configured to capture tomographic images of the retina of the subject eye. The anterior part OCT 53 is an optical coherence tomographic device (SS-OCT) comprising a wavelength sweeping light source 82, and comprises an anterior part measurement optical system (86a, 86c, 59, 60, 62, 63, 76, 68), a first anterior part reference optical system (86a, 86d, 88, 94, 90, 96, 92), a second anterior part reference optical system (80, 74), an anterior part interference optical system 88, and an anterior part detector 84.

The anterior part measurement optical system comprises optical fibers 86a, 86c, a coupler 88, a lens 59, a beam splitter 60, a Galvano scanner 62, a mirror 63, a lens 76, and a mirror 68. Light outputted from the light source 82 travels through the optical fiber 86a and is split into measurement light and first reference light in the coupler 88, and the measurement light split in the coupler 88 is outputted from the end of the optical fiber 86c toward the lens 59. The measurement light outputted to the lens 59 is emitted to the subject eye 200 (FIG. 7) via the beam splitter 60, the Galvano scanner 62, the mirror 63, the lens 76, and the mirror 68. In FIG. 5, a calibration tool 72 (such as a simulated eye) that is used as a substitute to the subject eye 200 at the time of product shipment is shown. The calibration tool 72 has a sheet of glass block at the position of the cornea and a sheet of glass block at the position of the retina. A thickness of each glass block (optical path length difference) and a distance between the two sheets of glass block (optical path length difference) are known. In the second embodiment as well, the Galvano scanner 62 is driven to scan the light emitted to the subject eye 200. The light reflected on the subject eye travels on the aforementioned path in an opposite direction and is inputted to the coupler 88.

The first anterior part reference optical system comprises optical fibers 86a, 86d, the coupler 88, a lens 94, a beam splitter 90, a lens 96, and a reference mirror 92. First reference light split by the coupler 88 is outputted from the end of the optical fiber 86d toward the lens 94, and is emitted to the reference mirror 92 via the beam splitter 90 and the lens %. Light reflected on the reference mirror 92 travels on the aforementioned path in an opposite direction and is inputted to the coupler 88.

The second anterior part reference optical system comprises an optical path branching from the anterior part measurement optical system (more specifically, a Galvano scanner 62), and comprises a lens 80 and a reference mirror 74 arranged on this optical path. The reference mirror 74 has the same configuration as the calibration tool 72 used at the time of product shipment, and is arranged such that an optical path length from the Galvano scanner 62 to the calibration tool 72 (more specifically, to a reflection surface of the glass block of the calibration tool 72 corresponding to the anterior surface of the cornea) match an optical path length from the Galvano scanner 62 to a reflection surface of the reference mirror 74 (more specifically, to a reflection surface of a glass block of the reference mirror 74 corresponding to the anterior surface of the cornea). Thus, so long as the optical path lengths of the optical systems of the anterior part OCT 53 do not change, a depthwise position of the reflection surface of the calibration tool 72 matches a depthwise position of the reference mirror 74. Similar to the first embodiment, a state in which the light from the light source 82 is emitted to the subject eye (calibration tool 72) and a state in which the light from the light source 82 is emitted to the reference mirror 74 are switched by driving the Galvano scanner 62. The light emitted to the reference mirror 74 is reflected toward the Galvano scanner 62, and is inputted to the coupler 88 through the beam splitter 60, the lens 59, and the optical fiber 86c.

The anterior part interference optical system comprises the coupler 88. The coupler 88 is configured to combine the light reflected from the calibration tool 72 (or the subject eye 200) and the light reflected from the reference mirror 92 and generate interference light, and to combine the light reflected from the reference mirror 74 and the light reflected from the reference mirror 92 and generate interference light. The interference light generated in the coupler 88 is inputted to the anterior part detector 84. The anterior part detector 84 is configured to detect the interference light and outputs an interference signal to a controller 100 (shown in FIG. 8).

The retina OCT 52 is an optical coherence tomographic device (SD-OCT) comprising a wide-band wavelength light source 54, and comprises a retina measurement optical system (58a, 58e, 55, 60, 62, 63, 66, 70, 76, 78, 68), a first retina reference optical system (58a, 58c, 58d, 55, 61, 64), a second retina reference optical system (58f, 61, 90, 96, 92), a retina interference optical system 55, and a retina detector 56.

The retina measurement optical system comprises optical fibers 58a, 58e, a coupler 55, the beam splitter 60, the Galvano scanner 62, mirrors 63, 66, 70, the lenses 76, 78, and the mirror 68. Light outputted from the light source 54 travels through the optical fiber 58a and is split into measurement light and third reference light in the coupler 55, and the measurement light split in the coupler 55 is outputted from the end of the optical fiber 58e toward the beam splitter 60. The light outputted from the optical fiber 58e is reflected on the beam splitter 60 and is outputted to the Galvano scanner 62. The light reflected on the Galvano scanner 62 is reflected on the mirrors 63, 66, 70, reflected on the mirror 68 through the lens 78, and is emitted onto the subject eye 200 (calibration tool 72 in FIG. 5). The reflected light from the subject eye 200 travels on the aforementioned path in an opposite direction and is inputted to the coupler 55.

The first retina reference optical system comprises optical fibers 58*a*, 58*c*, 58*d*, a coupler 55, 61, and a reference mirror 64. The third reference light split in the coupler 55 travels through the optical fiber 58*c* and is inputted to the coupler 61. The coupler 61 splits the light inputted from the optical fiber 58*c* into third reference light and fourth reference light (for example, third reference light: fourth reference light=99:1). The third reference light split in the coupler 61 travels through the optical fiber 58*d* and is outputted toward the reference mirror 64 from the end of the optical fiber 58*d*. The light outputted to the reference mirror 64 and reflected thereon travels on the aforementioned path in an opposite direction and is inputted to the coupler 55.

The second retina reference optical system has an optical path branching from the coupler 61 of the first retina reference optical system, and includes the coupler 61, an optical fiber 58*f*, a beam splitter 90, a lens 96, and a reference mirror 92 (the reference mirror 92 in the anterior part OCT 53). That is, the reference mirror 92 of the second retina reference optical system and the reference mirror 92 of the first anterior part reference optical system are a shared component. The fourth reference light split in the coupler 61 is emitted to the reference mirror 92 through the optical fiber 58*f*, the beam splitter 90, and the lens 96, and is reflected on the reference mirror 92. The fourth reference light reflected on the reference mirror 92 is inputted to the lens 96, the beam splitter 90, the optical fiber 58*f*, and the coupler 61. In the coupler 61, the third reference light reflected on the reference mirror 64 and the fourth reference light reflected on the reference mirror 92 are combined.

The retina interference optical system comprises the coupler 55. The coupler 55 combines the light inputted from the optical fiber 58*c* (that is, the third reference light reflected on the reference mirror 64 and the fourth reference light reflected on the reference mirror 92) and the light inputted from the optical fiber 58*e* (measurement light reflected on the subject eye). Due to this, interference light generated from the third reference light reflected on the reference mirror 64 and the measurement light reflected on the subject eye 200, interference light generated from the third reference light reflected on the reference mirror 64 and the fourth reference light reflected on the reference mirror 92, and interference light generated from the fourth reference light reflected on the reference mirror 92 and the measurement light reflected on the subject eye 200 are thereby generated. The generated interference light is inputted to the retina detector 56 through the optical fiber 58*b*. Here, an intensity of the fourth reference light is set to an intensity that is small enough that it can be ignored as compared to an intensity of the third reference light. Due to this, the retina detector 56 detects the interference light generated from the third reference light reflected on the reference mirror 64 and the measurement light reflected on the subject eye and also the interference light generated from the third reference light reflected on the reference mirror 64 and the fourth reference light reflected on the reference mirror 92, and outputs interference signals of the interference light as above to the controller 100 (shown in FIG. 8) to be described later.

Figure 8:
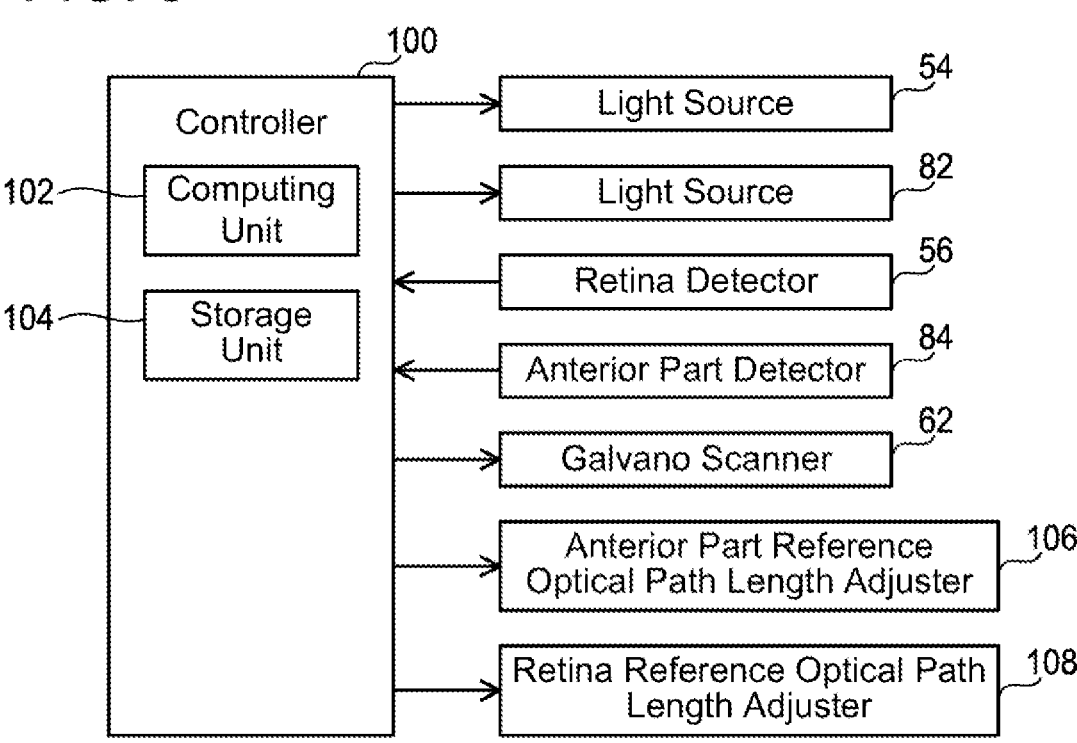
FIG. 8 is a block diagram showing a configuration of a control system of the ophthalmic device according to the second embodiment.

Next, the configuration of a control system of the ophthalmic device 50 will be described. As shown in FIG. 8, the ophthalmic device 50 is controlled by the controller 100. The controller 100 is configured of a microcomputer (microprocessor) configured of, for example, a CPU, a ROM, and a RAM, and functions as a computing unit 102 and a storage unit 104 similar to the first embodiment. The controller 100 includes the light sources 54, 82, the detectors 56, 84, and the Galvano scanner 62 connected thereto. The controller 100 is configured to control on/off of the light sources 54, 82 and also drive the Galvano scanner 62. Further, the controller 100 is configured to generate tomographic images of the subject eye 200 based on the interference signals inputted from the detectors 56, 84.

In the second embodiment, the controller 100 further includes an anterior part reference optical path length adjuster 106 and a retina reference optical path length adjuster 108 connected thereto. That is, in the second embodiment, a length from the end of the optical fiber 86*d* to the reference mirror 92 is adjustable, and a length from the end of the optical fiber 58*d* to the reference mirror 64 is adjustable. The controller 100 drives the anterior part reference optical path length adjuster 106 to move the lens 94, the beam splitter 90, the lens 96, and the reference mirror 92 in an optical axis direction with respect to the end of the optical fiber 86*d*. Further, the controller 100 drives the retina reference optical path length adjuster 108 to move the lens reference mirror 64 in the optical axis direction with respect to the end of the optical fiber 58*d*.

Further, the storage unit 104 of the controller 100 stores various types of information used for measuring the axial length of the subject eye 200. That is, in the ophthalmic device 50 of the second embodiment, as shown in FIG. 5, the calibration process is performed using the calibration tool 72 at the time of shipping, and various types of information obtained in this calibration process is stored in the storage unit 104. Specifically, the calibration tool 72 is arranged at the position of the subject eye 200, and positions of the front and rear surfaces of the glass block arranged at the position of the front surface of the calibration tool 72 (corresponding to the corneal surface) and the front and rear surfaces of the glass block arranged at the rear surface of the calibration tool 72 (corresponding to the retinal surface) are measured. That is, the positions of the front and rear surfaces of the glass block of the front surface of the calibration tool 72 (corresponding to the corneal surface) are measured using the anterior part OCT 53, and the positions of the front and rear surfaces of the glass block of the rear surface of the calibration tool 72 (corresponding to the retinal surface) are measured using the retina OCT 52. In doing so, the anterior part OCT 53 measures the position of the reflection surface of the reference mirror 74 in the second anterior part reference optical system. Further, the retina OCT 52 measures the position of the reference mirror 92 of the second retina reference optical system (that is, the reference mirror 92 in the first anterior part reference optical system of the anterior part OCT 53).

Here, the length from the front surface to the rear surface of the calibration tool 72 is known, thus similar to the first embodiment, the computing unit 102 of the controller 100 calculates conversion formulas and a positional relationship (length A) for calculating the axial length of the subject eye 200 (actual length thereof) from the position of the anterior surface of the cornea identified from the images captured in the anterior part OCT 53 and the position of the retinal surface identified from the images captured in the retina OCT 52. Then, the storage unit 104 of the controller 100 stores the calculated conversion formulas and positional relationship (length A). Further, the storage unit 104 of the controller 100 stores the measured position of the front surface of the calibration tool 72 (that is, the position of the reference mirror 74 in the second anterior part reference optical system) and the measured position of the reference mirror 92 (that is, the position of the reference mirror 92 in the second retina reference optical system).

Figure 9:
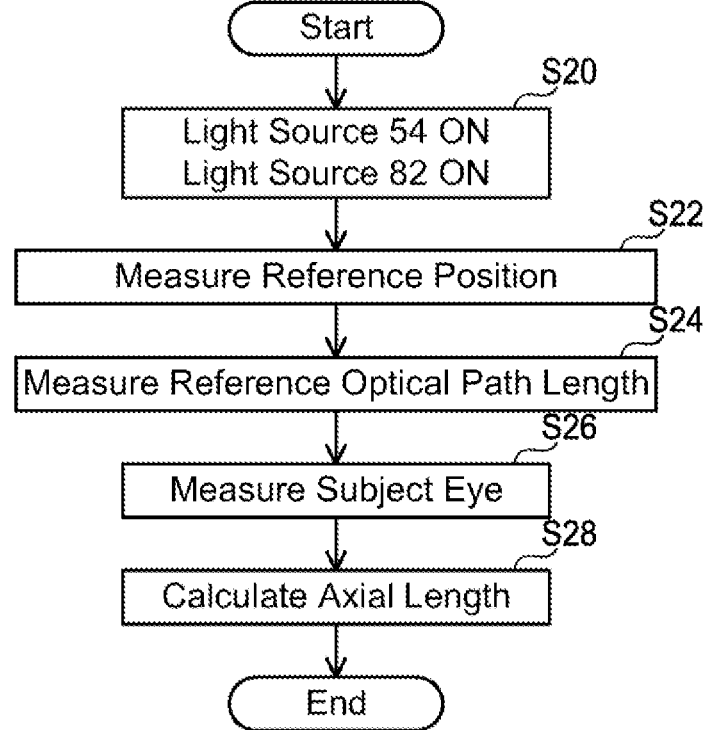
FIG. 9 is a flowchart showing a procedure for measuring the axial length of the subject eye using the ophthalmic device according to the second embodiment.

Next, operation of the ophthalmic device 50 at the time of measuring the axial length of the subject eye 200 will be described. Firstly, after the optical systems of the anterior part OCT 53 and the retina OCT 52 are positioned with respect to the subject eye 200, the controller 100 turns on the light sources 54, 82 as shown in FIG. 9 (S20).

Then, the controller 100 measures the position of the reference mirror 74 and the position of the reference mirror 92 (S22). Specifically, as shown in FIG. 6, the light from the light source 54 is emitted to the reference mirror 92, and the light from the light source 82 is emitted to the reference mirror 74 by driving the Galvano scanner 62. By doing so, the retina detector 56 detects the interference light that is generated from the reflected light reflected on the reference mirror 92 and the third reference light (third reference light in the first retina reference optical system), and the controller 100 calculates the position of the reference mirror 92 (reference mirror 92 in the first anterior part reference optical system) from the interference light detected by the retina detector 56. Further, the anterior part detector 84 detects the interference light that is generated from the reflected light reflected on the reference mirror 74 and the first reference light (first reference light in the first anterior part reference optical system), and the controller 100 calculates the position of the reference mirror 74 from the interference light detected by the anterior part detector 84.

Next, the controller 100 adjusts the optical path length of the first anterior part reference optical system and the optical path length of the first retina reference optical system based on the positions of the reference mirrors 74, 92 stored in the storage unit 104 and the positions of the reference mirrors 74, 92 measured in S22 (S24). As already described, the position of the front surface of the calibration tool 72 (that is, the position of the reference mirror 74) and the position of the reference mirror 92 are already measured in the calibration process at the time of shipment, and these are stored in the storage unit 104. The optical path lengths of the optical systems of the ophthalmic device 50 change from their values at the time of shipment (the time at which the calibration process is performed) due to the post-shipment chronological change and the environment temperature of the ophthalmic device 50. Due to this, in S24, the anterior part reference optical path length adjuster 106 adjusts the position of the reference mirror 92 so that the position of the reference mirror 92 measured in S22 matches the position of the reference mirror 92 stored in the storage unit 104. Next, the position of the reference mirror 64 is adjusted by the retina reference optical path length adjuster 108 so that the position of the reference mirror 74 measured in S22 matches the position of the front surface of the calibration tool 72 stored in the storage unit 104. At this occasion, since the position of the reference mirror 92 has already been adjusted, the position of the reference mirror 74 measured in S22 has changed according to this adjustment. Due to this, the position of the reference mirror 64 is adjusted based on the amount of the position adjustment of the reference mirror 92 and the position of the reference mirror 74 measured in S22. Due to this, a depthwise positional relationship of an imaging range 202a of the anterior part OCT 53 and an imaging range 204a of the retina OCT 52 matches the positional relationship at the time of the calibration process.

Next, as shown in FIG. 7, the controller 100 measures the position of the corneal surface of the subject eye 200 using the anterior part OCT 53 and measures the position of the retinal surface using the retina OCT 52 (S26). Then, the controller 100 uses the measurement results of S26 (the position of the corneal surface and the position of the retinal surface) and the conversion formulas and the positional relationship (length A) stored in the storage unit to calculate the axial length of the subject eye 200 (S28). Here, by S24, the depthwise positional relationship of the imaging range 202a of the anterior part OCT 53 and the imaging range 204a of the retina OCT 52 become identical to the positional relationship at the time of the calibration process. Due to this, the axial length can be calculated using the conversion formulas and the positional relationship (length A) stored in the storage unit without correcting the position of the corneal surface and the position of the retinal surface measured in S26.

In the ophthalmic device 50 of the second embodiment as above, the axial length of the subject eye 200 can be measured in the same state as the state at the time of the calibration by adjusting the optical path lengths of the optical systems of the anterior part OCT 53 and the retina OCT 52. Due to this, the ophthalmic device 50 of the second embodiment can also measure the axial length of the subject eye 200 with high accuracy.

Further, in the ophthalmic device 50 of the second embodiment as well, the measurement of the subject eye 200 is performed with the anterior part OCT 53 after the measurement of the reference mirror 74 has been completed. That is, since the measurement of the reference mirror 74 and the measurement of the subject eye 200 are not performed simultaneously, the position of the reference mirror 74 can be set to a desired position.

In the ophthalmic device 50 of the second embodiment as above, the reference optical path length of the first anterior part reference optical system in the anterior part OCT 53 as well as the reference optical path length of the first retina reference optical system in the retina OCT 52 are adjusted such that the positional relationship of the anterior part OCT 53 and the retina OCT 52 matches the positional relationship in the calibration process, however, the art disclosed herein is not limited to such an example. For example, only the reference optical path length of the first anterior part reference optical system in the anterior part OCT 53 may be adjusted such that the positional relationship of the anterior part OCT 53 and the retina OCT 52 matches the positional relationship in the calibration process. Alternatively, the positional relationship of the anterior part OCT 53 and the retina OCT 52 may be set to match the positional relationship in the calibration process by adjusting only the reference optical path length of the first retina reference optical system in the retina OCT 52.

Further, in the ophthalmic device 50 of the second embodiment, the third reference light in the retina OCT 52 is split to generate fourth reference light, and the generated fourth reference light is emitted to the reference mirror 92, however, the art disclosed herein is not limited to such an example. Contrary to the aforementioned example, the first reference light in the anterior part OCT may be split to generate the second reference light, and this generated second reference light may be emitted to the reference mirror 64.

Further, the ophthalmic devices in the first and second embodiments as above each comprise both the retina OCT and the anterior part OCT, however, the art disclosed herein may be applied to ophthalmic devices that comprise only the retina OCT or the anterior part OCT. In such a case, for example, a state in which light from a light source is emitted to a reference mirror and a state in which the light from the light source is emitted to the subject eye can be switched using a Galvano scanner, by which the reference mirror can be set to a desired position.

Specific examples of the disclosure herein have been described in detail, however, these are mere exemplary indications and thus do not limit the scope of the claims. The art described in the claims includes modifications and variations of the specific examples presented above. Technical features described in the description and the drawings may technically be useful alone or in various combinations, and are not limited to the combinations as originally claimed. Further, the purpose of the examples illustrated by the present description or drawings is to satisfy multiple objectives simultaneously, and satisfying any one of those objectives gives technical utility to the present disclosure.

What is claimed is:

1. An ophthalmic device comprising:
a light source;
a measurement optical system configured to generate measurement light by irradiating a subject eye with light from the light source;
a first reference optical system configured to generate first reference light by using the light from the light source;
a second reference optical system configured to generate second reference light by using the light from the light source, the second reference light being used for calculating a reference position;
an interference optical system configured to generate measurement interference light by combining the measurement light and the first reference light and to generate reference interference light by combining the second reference light and the first reference light;
a detector configured to detect the measurement interference light and output a measurement interference signal and to detect the reference interference light and output a reference interference signal; and
a controller configured to calculate depthwise position information of the subject eye based on the measurement interference signal and to calculate the reference position based on the reference interference signal, wherein
the second reference optical system includes an optical path branching from the measurement optical system,
the measurement optical system comprises a switching unit configured to switch between a first state and a second state, the first state being a state in which the subject eye is irradiated with the light from the light source and the second state being a state in which the light from the light source is guided to the second reference optical system,
when the subject eye is measured, the controller is configured to control the switching unit to detect the measurement interference light with the detector in the first state, and to detect the reference interference light with the detector in the second state, and0 wherein
the ophthalmic device further comprises a storage unit configured to store a specific-time reference position indicating the reference position adjusted at a specific time, the specific-time reference position being a position calculated from the reference interference light generated by combining the second reference light generated in the second reference optical system and the first reference light generated in the first reference optical system at the specific time, and the controller is configured to correct the depthwise position information of the subject eye calculated based on the measurement interference signal outputted from the detector when the subject eye is measured, the depthwise position information being corrected based on a difference between a measurement-time reference position and the specific-time reference position stored in the storage unit, the measurement-time reference position being the reference position calculated based on the reference interference signal outputted from the detector when the subject eye is measured.

2. The ophthalmic device according to claim 1, wherein the controller is configured to control the switching unit to detect the reference interference signal with the detector in the second state before or after detecting the measurement interference light with the detector in the first state.

3. The ophthalmic device according to claim 1, wherein the storage unit is configured to further store a conversion formula for converting the depthwise position information of the subject eye calculated based on the measurement interference signal to an actual measurement of the subject eye,
the controller is configured to further calculate the actual measurement of the subject eye by converting the depthwise position information of the subject eye calculated based on the measurement interference signal with the conversion formula, and
the conversion formula is obtained by using (A) depthwise position information of at least two reflection surfaces of a calibration tool having a known optical path length difference and (B) the optical path length difference between the at least two reflection surfaces, the depthwise position information of the at least two reflection surfaces being obtained from calibration interference light generated by combining calibration measurement light and the first reference light generated in the first reference optical system, the calibration measurement light being generated by irradiating the calibration tool from the measurement optical system with the light from the light source.

4. The ophthalmic device according to claim 3, wherein the specific time and a time at which the calibration interference light is measured by using the calibration tool to obtain the conversion formula are substantially simultaneous.

5. An ophthalmic device comprising;
a light source;
a measurement optical system configured to generate measurement light by irradiating a subject eye with light from the light source;
a first reference optical system configured to generate first reference light by using the light from the light source;
a second reference optical system configured to generate second reference light bv using the light from the light source, the second reference light being used for calculating a reference position;
an interference optical system configured to generate measurement interference light by combining the measurement light and the first reference light and to generate reference interference light by combining the second reference light and the first reference light,
a detector configured to detect the measurement interference light and output a measurement interference signal and to detect the reference interference light and output a reference interference signal, and a controller configured to calculate depthwise position information of the subject eye based on the measurement interference signal and to calculate the reference position based on the reference interference signal, wherein the second reference optical system includes an optical path branching from the measurement optical system, the measurement optical system comprises a switching unit configured to switch between a first state and a second state, the first state being a state in which the subject eve is irradiated with the light from the light source and the second state being a state in which the light from the light source is guided to the second reference optical system, when the subject eve is measured, the controller is configured to control the switching unit to defect the measurement interference light with the detector in the first state, and to detect the reference interference light with the detector in the second state, and wherein the ophthalmic device further comprises a storage unit configured to store a specific-time reference position indicating the reference position adjusted at a specific time, the specific-time reference position being a position calculated from the reference interference light generated by combining the second reference light generated in the second reference optical system and the first reference light generated in the first reference optical system at the specific time, wherein the first reference optical system comprises an adjuster configured to adjust an optical path length of the first reference light, and the controller is configured to calculate a measurement-time reference position that is the reference position calculated based on the reference interference signal outputted from the detector when the subject eye is measured and to control the adjuster so that the measurement-time reference position calculated when the subject eye is measured matches the specific-time reference position stored in the storage unit.

6. The ophthalmic device according to claim 5, wherein the storage unit is configured to further store a conversion formula for converting the depthwise position information of the subject eye calculated based on the measurement interference signal to an actual measurement of the subject eye, the controller is configured to further calculate the actual measurement of the subject eye by converting the depthwise position information of the subject eye calculated based on the measurement interference signal with the conversion formula, and the conversion formula is obtained by using (A) depthwise position information of at least two reflection surfaces of a calibration tool having a known optical path length difference and (B) the optical path length difference between the at least two reflection surfaces, the depthwise position information of the at least two reflection surfaces being obtained from calibration interference light generated by combining calibration measurement light and the first reference light generated in the first reference optical system, the calibration measurement light being generated by irradiating the calibration tool from the measurement optical system with the light from the light source.

7. The ophthalmic device according to claim 6, wherein the specific time and a time at which the calibration interference light is measured by using the calibration tool to obtain the conversion formula are substantially simultaneous.

8. The ophthalmic device according to claim 5, wherein the controller is configured to:

detect the reference interference light with the detector while the switching unit is in the second state;

control the adjuster so that the measurement-time reference position calculated based on the reference interference signal outputted from the detector matches the specific-time reference position stored in the storage unit; and detect the measurement interference light while the switching unit is in the first state after the optical path length of the first reference light is adjusted by the adjuster.

9. An ophthalmic device comprising:

a first OCT configured to measure a first depthwise position of a first part of a subject eye;

a second OCT configured to measure a second depthwise position of a second part of the subject eye, the second part being different from the first part; and a controller configured to calculate a depthwise length from the first part to the second part based on the first depthwise position measured by the first OCT and the second depthwise position measured by the second OCT, wherein the first OCT comprises:

a first light source;

a first measurement optical system configured to generate first measurement light by irradiating the first part of the subject eye with light from the first light source;

a first reference optical system configured to generate first reference light by using the light from the first light source;

a second reference optical system configured to generate second reference light by using the light from the first light source, the second reference light being used for calculating a first reference position;

a first interference optical system configured to generate first measurement interference light by combining the first measurement light and the first reference light and to generate first reference interference light by combining the second reference light and the first reference light; and a first detector configured to detect the first measurement interference light and output a first measurement interference signal and to detect the first reference interference light and output a first reference interference signal, wherein the second reference optical system includes an optical path branching from the first measurement optical system, the first measurement optical system comprises a first switching unit configured to switch between a first state and a second state, the first state being a state in which the subject eye is irradiated with the light from the first light source and the second state being a state in which the light from the first light source is guided to the second reference optical system, when the subject eye is measured, the first detector is configured to detect the first measurement interference light while the first switching unit is in the first state, and to detect the first reference interference light while the first switching unit is in the second state, wherein the second OCT comprises:

a second light source;

a second easurement optical system configured to generate second measurement light by irradiating the second part of the subject eye with light from the second light source;

a third reference optical system configured to generate third reference light by using the light from the second light source;

a fourth reference optical system configured to generate fourth reference light by using the light from the second light source, the fourth reference light being used for calculating a second reference position;

a second interference optical system configured to generate second measurement interference light by combining the second measurement light and the third reference light and to generate second reference interference light by combining the fourth reference light and the third reference light; and a second detector configured to detect the second measurement interference light and output a second measurement interference signal and to detect the second reference interference light and output a second reference interference signal, wherein the fourth reference optical system includes an optical path branching from the second measurement optical system, the second me asurement optical system comprises a second switching unit configured to switch between a third state and a fourth state, the third state being a state in which the subject eve is irradiated with the light from the second light source and the fourth state being a state in which the light from the second light source is guided to the fourth reference optical system, and when the subject eve is measured, the second detector is configured to detect the second measurement interference light while the second switching onit is in the third state, and to detect the second reference interference light while the second switching unit is in the fourth state, the ophthalmic device further comprises a storage unit configured to store a depthwise distance between a measurement area of the first OCT and a measurement area of the second OCT adjusted at a specific time, a first specific-time reference position indicating the first reference position adjusted at the specific time, and a second specific-time reference position indicating the second reference position adjusted at the specific time, and wherein the controller is configured to calculate the depthwise length from the first part to the second part based on:

(1) a difference between a first measurement-time reference position and the first specific-time reference position stored in the storage unit, the first measurement-time reference position being calculated based on the first reference interfence signal outputted from the first detector when the subject eye is measured;

(2) the first position of the subject eve calculated based on the first measurement interference signal outputted from the first detector when the subject eye is measured;

(3) a difference between a second measurement-time reference position and the second specific-time reference position stored in the storage unit, the second measurement-time reference position being calculated based on the second reference interference signal outputted from the second detector when the subject eye is measured;

(4) the second position of the subject eye calculated based on the second measurement interference signal outputted from the second detector when the subject eve is measured, and (5) the depthwise distance between the measurement area of the first OCT and the measurement area of the second OCT stored in the storage unit.

10. The ophthalmic device according to claim 9, wherein when the first switching unit is switched to the first state, the second switching unit is switched to the third state, when the first switching unit is switched to the second state, the second switching unit is switched to the fourth state, and the first switching unit and the second switching unit are a single switching unit shared by the first measurement optical system and the second measurement optical system.

11. The ophthalmic device according to claim 9, wherein the storage unit is configured to further store:

a first conversion formula for converting depthwise position information of the subject eye calculated based on the first measurement interference signal to an actual measurement of the subject eye in the measurement area of the first OCT; and a second conversion formula for converting depthwise position information of the subject eye calculated based on the second measurement interference signal to an actual measurement of the subject eye in the measurement area of the second OCT, wherein the controller is configured to further calculate the actual measurement of the subject eye in the measurement area of the first OCT by converting the depthwise position information of the subject eye calculated based on the first measurement interference signal with the first conversion formula, and to further calculate the actual measurement of the subject eye in the measurement area of the second OCT by converting the depthwise position information of the subject eye calculated based on the second measurement interference signal with the second conversion formula, the first conversion formula is obtained by using (A1) depthwise position information of at least two reflected surfaces of a first calibration tool having a known an optical path length difference and (B1) the optical path length difference between the at least two reflected surfaces, the depthwise position information of the at least two reflected surfaces of the first calibration tool is obtained from first calibration interference light generated by combining first calibration measurement light and first reference light generated in the first reference optical system, the first calibration measurement light being generated by irradiating the first calibration tool from the first measurement optical system with the light from the first light source, and the second conversion formula is obtained by using (A2) depthwise position information of at least two reflected surfaces of a second calibration tool having a known optical path length difference and (B2) the optical path length difference between the at least two reflected surfaces, the depthwise position information of the at least two reflected surfaces of the second calibration tool is obtained from second calibration interference light generated by combining second calibration measurement light and third reference light generated in the third reference optical system, the second calibration measurement light is generated by irradiating the second calibration tool from the second measurement optical system with the light from the second light source.

12. The ophthalmic device according to claim 11, wherein the first specific-time reference position is a position calculated from the first reference interference light generated by combining the second reference light generated in the second reference optical system and the first reference light generated in the first reference optical system at the specific time, the second specific-time reference position is a position calculated from the second reference interference light generated by combining the fourth reference light generated in the fourth reference optical system and the third reference light generated in the third reference optical system at the specific time, and the specific time, a time at which the first calibration tool is irradiated with the first measurement light to obtain the first conversion formula and a time at which the second calibration tool is irradiated to the second measurement light to obtain the second conversion formula are substantially simultaneous.

13. The ophthalmic device according to claim 9, further comprising an adjuster disposed on at least one of the first reference optical system and the third reference optical system and configured to adjust an optical path length of the at least one of the first reference optical system and the third reference optical system, wherein
the controller is configured to control the adjuster so that a distance between a first measurement-time reference position calculated from the first reference interference signal when the subject eye is measured and a second measurement-time reference position calculated from the second reference interference signal when the subject eye is measured matches a predetermined distance.

14. The ophthalmic device according to claim 13, wherein the predetermined distance is a distance between a first specific-time reference position calculated from the first reference interference signal at a specific time and a second specific-time reference position calculated from the second reference interference signal at the specific time.

15. The ophthalmic device according to claim 13, wherein the controller is configured to:

detect the first reference interference light with the first detector while the first switching unit is in the second state;

detect the second reference interference light with the second detector while the second switching unit is the fourth state;

control the adjuster so that a difference between the first measurement-time reference position calculated based on the first reference interference signal outputted from the first detector and the second measurement-time reference position calculated based on the second reference interference signal outputted from the second detector matches the predetermined distance, and after the optical path length is adjusted by the adjuster, detect the first measurement interference signal while the first switching unit is in the first state, and detect the second measurement interference signal while the second switching unit is in the third state.

* * * * *